(12) United States Patent
Iida et al.

(10) Patent No.: US 6,504,154 B2
(45) Date of Patent: Jan. 7, 2003

(54) NON-DESTRUCTIVE SUGAR CONTENT MEASURING APPARATUS

(75) Inventors: Junji Iida, Chiba (JP); Akira Terashima, Chiba (JP); Kazuo Maeda, Chiba (JP); Shintaro Ishikawa, Chiba (JP); Shinji Yamauchi, Chiba (JP)

(73) Assignee: Sumitomo Metal Mining Co., Ltd., Tokyo (JP)

( * ) Notice: Subject to any disclaimer, the term of this patent is extended or adjusted under 35 U.S.C. 154(b) by 37 days.

(21) Appl. No.: 09/783,994

(22) Filed: Feb. 16, 2001

(65) Prior Publication Data

US 2001/0045517 A1 Nov. 29, 2001

(30) Foreign Application Priority Data

Apr. 24, 2000 (JP) ........................................ 2000-122459
Dec. 21, 2000 (JP) ........................................ 2000-388620

(51) Int. Cl.⁷ .............................................. G01N 21/35
(52) U.S. Cl. .................................................. 250/339.06
(58) Field of Search ........................ 250/339.06, 339.12

(56) References Cited

U.S. PATENT DOCUMENTS

| 5,089,701 A | 2/1992 | Dull et al. |
| 5,708,271 A | 1/1998 | Ito et al. |
| 5,726,750 A | 3/1998 | Ito et al. |
| 5,844,678 A | * 12/1998 | Ito et al. ................ 356/244 |

FOREIGN PATENT DOCUMENTS

| JP | 6-258225 | 9/1964 |
| JP | 1-216265 | 8/1989 |
| JP | 1-235850 | 9/1989 |
| JP | 1-284758 | 11/1989 |
| JP | 2-147940 | 6/1990 |
| JP | 4-104041 | 4/1992 |
| JP | 4-115142 | 4/1992 |
| JP | 4-116503 | 4/1992 |
| JP | 4-208842 | 7/1992 |
| JP | 5-34281 | 2/1993 |
| JP | 5-142036 | 6/1993 |
| JP | 5-172549 | 7/1993 |
| JP | 6-15236 | 1/1994 |
| JP | 9-15142 | 1/1997 |

* cited by examiner

*Primary Examiner*—Constantine Hannaher
*Assistant Examiner*—Shun Lee
(74) *Attorney, Agent, or Firm*—Armstrong, Westerman & Hattori, LLP

(57) ABSTRACT

A non-destructive sugar content measuring apparatus having a plurality of trays on which vegetables and fruits are to be placed, a transport device for successively delivering the trays at appropriate intervals, and first, second and third measuring sections provided in the course of a transport path and at which laser beams having wavelengths $\lambda 1$, $\lambda 2$ and $\lambda 3$ are respectively made incident on each vegetable or fruit and the amount of light of each laser beam emergent from the vegetable or fruit is measured with a detector provided at each measuring section and the absorbance of each laser beam is determined from the amount of incident light made incident on the vegetable or fruit and the amount of detected light which has been measured with the detector, to measure the sugar content of the vegetables and fruits on the basis of each absorbance.

12 Claims, 14 Drawing Sheets

SUGAR CONTENT VARIATIONS WITH DEVIATION OF WAVELENGTH

NON-DESTRUCTIVE SUGAR CONTENT MEASURING APPARATUS

BACKGROUND OF THE INVENTION

1. Field of the Invention

This invention relates to a non-destructive sugar content measuring apparatus applied to vegetables and fruits such as muskmelons, watermelons pumpkins and oranges and with which their sugar content can be measured without destroying the vegetables and fruits. More particularly, it relates to an improvement of the non-destructive sugar content measuring apparatus, which can measure the sugar content at an error within plus-minus 0.5 brix whenever the same vegetables and fruits kept at a constant temperature are measured (i.e., have measurement reproducibility).

2. Description of the Related Art

As methods for measuring the sugar content of vegetables and fruits without destroying them, methods are known in which near-infrared light or infrared light is made incident on vegetables and fruits to determine the sugar content by measuring the absorption of light by sugar on the basis of reflected light or transmitted light of the incident light (see Japanese Patent Applications Laid-open No. 1-216265, No. 1-235850, No. 2-147940, No. 4-104041, No. 4-208842, No. 5-34281, No. 5-172549 and No. 6-15236).

These methods, however, all make use of halogen lamps as light sources. Hence, light intensity is insufficient for vegetables and fruits having a thick rind, and it has been difficult to measure their sugar content.

Accordingly, as a method which can eliminate such a disadvantage, the applicant has already proposed a method in which three laser beams having different wavelengths are applied and at the same time the respective laser beams are successively made incident on vegetables and fruits such as muskmelons, watermelons pumpkins and oranges at substantially the same positions on their rinds.

To describe this measuring method briefly, as shown in FIG. 17 a laser beam having a wavelength $\lambda$ is made incident on a fruit M such as a muskmelon, e.g., from its lower side, and also the laser beam having a wavelength $\lambda$ which is emergent from the fruit M is detected with a detector (not shown) disposed similarly at the lower side. In FIG. 17, $Pin(\lambda)$ indicates the amount of incident light of the laser beam, and $Pout(\lambda)$ the amount of detected light of the laser beam.

Then, the sugar content (brix) of the fruit M can be determined from data of input signals $Pin(\lambda)'$ corresponding to the amount of incident light $Pin(\lambda)$ and output signals $Pout(\lambda)'$ corresponding to the amount of detected light $Pout(\lambda)$ and according to the following Equation (4).

More specifically, sugar content Y (brix) can be, in respect of the laser beams having three kinds of wavelengths, determined by substituting absorbance $X(\lambda)$:

$$X(\lambda) = -\log T(\lambda) \quad (2)$$

which is a natural logarithmic value of transmittance $T(\lambda)$ defined as:

$$T(\lambda) = Pout(\lambda)/Pin(\lambda) = (e2/e1)Pout(\lambda)'/Pin(\lambda)' \quad (3)$$

for Equation (4):

$$Y = AX(\lambda 1) + BX(\lambda 2) + CX(\lambda 3) + D \quad (4)$$

Here, A, B and C are constants which are determined on many fruits (samples) by, e.g., the method of least squares in such a way that the correlation comes to be highest between sugar content Y determined with a refraction saccharometer and absorbance $X(\lambda 1)$, $X(\lambda 2)$ and $X(\lambda 3)$ determined by photometry.

Incidentally, the amount of incident light $Pin(\lambda)$ and the output signals $Pin(\lambda)'$ corresponding thereto are correlated as $Pin(\lambda) = e1 \cdot Pin(\lambda)'$, and the amount of incident light $Pout(\lambda)$ and the output signals $Pout(\lambda)'$ corresponding thereto are correlated as $Pout(\lambda) = e2 \cdot Pout(\lambda)'$. Also, coefficients e1 and e2 are determined when the measuring apparatus is produced.

Then, from the values of electric signals $Pin(\lambda)'$ and $Pout(\lambda)'$, the sugar content Y (brix) is determined in the manner as described above.

To make description according to a conventional non-destructive sugar content measuring apparatus embodying this method, as shown in FIG. 18 the fruit M such as a muskmelon is placed on a tray d having two tray-side light passages g and h at its bottom and is transported. A laser beam having the amount of incident light Pin(1) is made incident on the fruit M from the leading end of an optical fiber w at each measuring section k provided in a transport path and having two measurement-side light passages i and j positionally adjusted to the tray-side light passages g and h of the tray d, through the measurement-side light passage i and tray-side light passage g. At the same time, the laser beam which has become emergent from the fruit M is made to enter each detector c through the tray-side light passage h and measurement-side light passage j to measure the output signals Pout(1)' corresponding to the amount of detected light Pout(1), where the sugar content is measured on the basis of these output signals Pout(1)' and input signals Pin(1)' corresponding to the amount of incident light Pin(1).

Incidentally, in FIG. 18, m denotes a linear projection which is so provided as to extend in the lengthwise direction in the transport path at the measuring section k and prevents the laser beam from entering the measurement-side light passage j when it passes through the measurement-side light passage i; n, a linear recession which is provided at the bottom (under side) of the tray d and is loosely fitted to the linear projection m; p, a first side bar as a delivery position control means for controlling delivery position of the tray d at each measuring section k; q, a second side bar as a delivery position control means for pressing the tray d to the first side bar p side to control delivery position of the tray d; and 300, a laser output monitoring means whose main part is constituted of an output monitoring detector 3a, a distributor 3b and a light diffusion plate 3c.

Now, when the sugar content of vegetables and fruits is measured by means of the non-destructive sugar content measuring apparatus of this type, the non-destructive sugar content measuring apparatus is demanded to measure the sugar content at an error within plus-minus 0.5 brix whenever the same vegetables and fruits kept at a constant temperature are measured, i.e., to have measurement reproducibility.

As factors which may obstruct this measurement reproducibility, what have conventionally been regarded are, e.g., a delicate change in laser output given from each laser light source, a poor ratio of noise to signal intensity (s/n ratio) at the time the light having transmitted through the interior of a fruit is converted into signals, and a roll of the tray or a sway of the fruit during measurement.

However, at any effort to devise the delivery position control means, the laser output monitoring means and so forth so as to remove such factors which may obstruct the measurement reproducibility, there has remained the problem that the measurement reproducibility in non-destructive sugar content measuring apparatus is still unsatisfactory.

Accordingly, the present inventors continued extensive studies in order to solve this problem. As a result, it has become revealed that, as a factor which may obstruct the measurement reproducibility of non-destructive sugar content measuring apparatus, a slight fluctuation in wavelength of laser beams emitted from laser light sources unexpectedly affects the accuracy of measurement to cause an error, in addition to the above various factors.

SUMMARY OF THE INVENTION

The present invention was made taking account of such a problem. Accordingly, an object of the present invention is to provide a non-destructive sugar content measuring apparatus which can measure the sugar content at an error within plus-minus 0.5 brix whenever the same vegetables and fruits kept at a constant temperature are measured (i.e., have measurement reproducibility).

Another object of the present invention is to provide a non-destructive sugar content measuring apparatus in which wavelengths $\lambda 1$, $\lambda 2$ and $\lambda 3$ of laser beams are selected from within the ranges of from 860 nm$\leq$wavelength $\lambda 1$<900 nm, 900 nm$\leq$wavelength $\lambda 2 \leq$920 nm, and 920 nm<wavelength $\lambda 3 \leq$960 nm, and which can measure the sugar content at an error within plus-minus 0.5 brix whenever the same vegetables and fruits kept at a constant temperature are measured.

Still another object of the present invention is to provide a non-destructive sugar content measuring apparatus in which wavelengths $\lambda 1$, $\lambda 2$ and $\lambda 3$ of laser beams are selected from within the ranges of from 800 nm$\leq$wavelengths $\lambda 1$ and $\lambda 2$<900 nm, and 900 nm$\leq$wavelength $\lambda 3 \leq$920 nm (provided that the wavelengths $\lambda 1$ and $\lambda 2$ have a wavelength distance between them of 10 nm or larger), and which can measure the sugar content at an error within plus-minus 0.5 brix whenever the same vegetables and fruits kept at a constant temperature are measured.

To achieve the above objects, the present invention is, as a first embodiment, a non-destructive sugar content measuring apparatus comprising a plurality of trays on which vegetables and fruits are to be placed, a transport means for successively delivering the trays at appropriate intervals, and first, second and third measuring sections provided in the course of a transport path and at which laser beams having wavelengths $\lambda 1$, $\lambda 2$ and $\lambda 3$ are respectively made incident on each vegetable or fruit and the amount of light of each laser beam emergent from the vegetable or fruit is measured with a detector provided at each measuring section and at the same time the absorbance of each laser beam is determined from the amount of incident light made incident on the vegetable or fruit and the amount of detected light which has been measured with the detector, to measure the sugar content of the vegetables and fruits on the basis of each absorbance thus determined wherein;

the wavelengths $\lambda 1$, $\lambda 2$ and $\lambda 3$ of the laser beams satisfy the conditions of:

860 nm$\leq$wavelength $\lambda 1$<900 nm, 900 nm$\leq$wavelength $\lambda 2 \leq$920 nm, 920 nm<wavelength $\lambda 3 \leq$960 nm, and, where standard deviations of wavelength variations in the wavelengths $\lambda 1$, $\lambda 2$ and $\lambda 3$ are represented by $\Delta\lambda 1$, $\Delta\lambda 2$ and $\Delta\lambda 3$, respectively, satisfy the condition of the following mathematical expression (1):

$$[f1(\lambda 1) \times \Delta\lambda 1 + f2(\lambda 2) \times \Delta\lambda 2 + f3(\lambda 3) \times \Delta\lambda 3] < 0.5 \text{ brix} \tag{1}$$

in which mathematical expression (1), $f1(\lambda 1)$, $f2(\lambda 2)$ and $f3(\lambda 3)$ respectively represent sugar content variation functions (brix/nm) determined from sugar content variation curves showing the relationship between the wavelength variations in the wavelengths $\lambda 1$, $\lambda 2$ and $\lambda 3$ and the sugar content variations that accompany the former.

The present invention is, as a second embodiment, a non-destructive sugar content measuring apparatus comprising a plurality of trays on which vegetables and fruits are to be placed, a transport means for successively delivering the trays at appropriate intervals, and first, second and third measuring sections provided in the course of a transport path and at which laser beams having wavelengths $\lambda 1$, $\lambda 2$ and $\lambda 3$ are respectively made incident on each vegetable or fruit and the amount of light of each laser beam emergent from the vegetable or fruit is measured with a detector provided at each measuring section and at the same time the absorbance of each laser beam is determined from the amount of incident light made incident on the vegetable or fruit and the amount of detected light which has been measured with the detector, to measure the sugar content of the vegetables and fruits on the basis of each absorbance thus determined wherein;

the wavelengths $\lambda 1$, $\lambda 2$ and $\lambda 3$ of the laser beams satisfy the conditions of:

800 nm$\leq$wavelengths $\lambda 1$, $\lambda 2$<900 nm, 900 nm$\leq$wavelength $\lambda 3 \leq$920 nm, the wavelengths $\lambda 1$ and $\lambda 2$ having a wavelength distance between them of 10 nm or larger; and, where standard deviations of wavelength variations in wavelengths $\lambda 1$, $\lambda 2$ and $\lambda 3$ are represented by $\Delta\lambda 1$, $\Delta\lambda 2$ and $\Delta\lambda 3$, respectively, satisfy the condition of the following mathematical expression (1):

$$[f1(\lambda 1) \times \Delta\lambda 1 + f2(\lambda 2) \times \Delta\lambda 2 + f3(\lambda 3) \times \Delta\lambda 3] < 0.5 \text{ brix} \tag{1}$$

in which mathematical expression (1), $f1(\lambda 1)$, $f2(\lambda 2)$ and $f3(\lambda 3)$ respectively represent sugar content variation functions (brix/nm) determined from sugar content variation curves showing the relationship between the wavelength variations in the wavelengths $\lambda 1$, $\lambda 2$ and $\lambda 3$ and the sugar content variations that accompany the former.

DESCRIPTION OF THE PREFERRED EMBODIMENTS

The present invention will be described below in detail.

Figure 13:
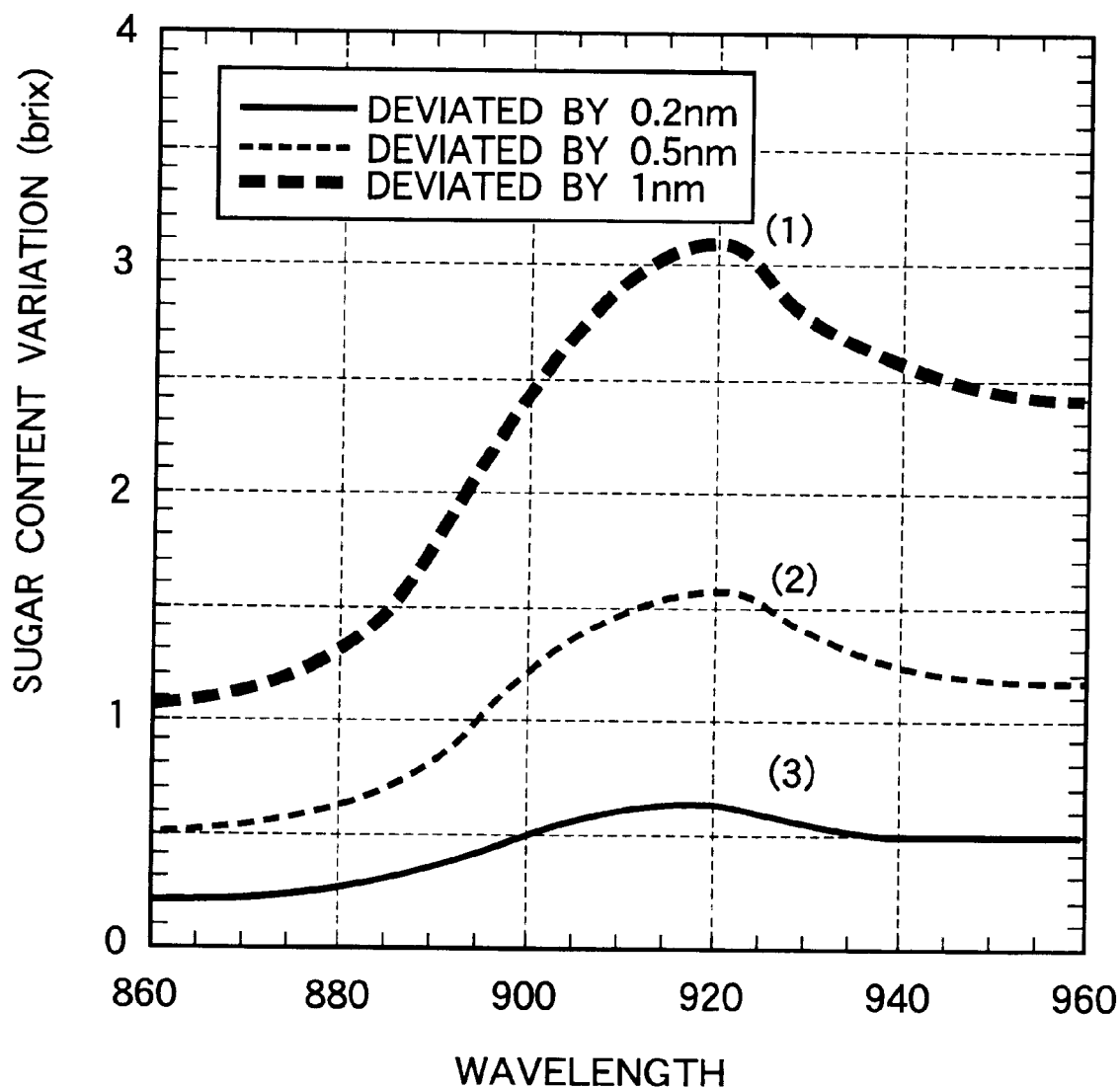
FIG. 13 is a graph showing sugar content variation curves where only one wavelength has been (1) deviated by 1 nm, (2) deviated by 0.5 nm and (3) deviated by 0.2 nm, among three wavelengths used in the non-destructive sugar content measuring apparatus in which the wavelengths $\lambda 1$, $\lambda 2$ and $\lambda 3$ of laser beams are selected from within the ranges of from 860 nm$\leq$wavelength $\lambda 1$<900 nm, 900 nm$\leq$wavelength $\lambda 2 \leq$920 nm, and 920 nm<wavelength $\lambda 3 \leq$960 nm.

Referring first to FIG. 13, it is a graphic representation of sugar content variation curves showing the relationship between the wavelength variations in the wavelengths $\lambda 1$, $\lambda 2$ and $\lambda 3$, determined in the manner as described below, and the sugar content variations that accompany the former.

More specifically, premised on a non-destructive sugar content measuring apparatus in which the wavelengths $\lambda 1$, $\lambda 2$ and $\lambda 3$ of laser beams are selected from within the ranges of:

860 nm$\leq$wavelength $\lambda 1$<900 nm, 900 nm$\leq$wavelength $\lambda 2 \leq$920 nm, 920 nm<wavelength $\lambda 3 \leq$960 nm, a titanium-sapphire laser was used as a laser light source, and a laser beam emitted from the laser light source was made incident on a fruit (muskmelon), varying the wavelengths of the laser beam, to determine what percent (%) its transmittance varies and also to determine, according to Equations (2) and (4) set forth previously, sugar content variations caused when the transmittance varies, where the results shown in FIG. 13 were obtained.

FIG. 13 is a graph showing sugar content variation curves where only one wavelength among the three wavelengths used has been (1) deviated by 1 nm, (2) deviated by 0.5 nm and (3) deviated by 0.2 nm. Then, it has been confirmed from the graph in FIG. 13 that the relationship between wavelength variations and sugar content variations stands linear when the wavelength variations are at least in an extent within the range of from 0.1 nm to 1 nm.

FIG. 13 shows sugar content variations caused when only one wavelength is varied among the three wavelengths used. However, since the three wavelengths are used in the measurement of sugar content with the non-destructive sugar content measuring apparatus, there may be a case in which sugar content variations caused by wavelength variations of all the three wavelengths are added.

Accordingly, in respect of the non-destructive sugar content measuring apparatus in which the wavelengths $\lambda 1$, $\lambda 2$ and $\lambda 3$ of laser beams are selected from within the ranges of:

860 nm$\leq$wavelength $\lambda 1$<900 nm, 900 nm$\leq$wavelength $\lambda 2 \leq$920 nm, 920 nm<wavelength $\lambda 3 \leq$960 nm, maximum values of sugar content variations in the respective wavelength regions are found on the basis of the FIG. 13 graph (sugar content variation curves), and the extent of wavelength variations in which the sugar content can be measured at an error within plus-minus 0.5 brix is determined from the sum of such maximum values.

More specifically, when the wavelengths vary in an extent of 1 nm, the maximum value of sugar content variations in the case of the wavelength $\lambda 1$ (860 nm$\leq$wavelength $\lambda 1$<900 nm) is found from (1) in FIG. 13 to be 2.5 brix, and also the maximum values of sugar content variations in the cases of the wavelength $\lambda 2$ (900 nm$\leq$wavelength $\lambda 2 \leq$920 nm) and wavelength $\lambda 3$ (920 nm<wavelength $\lambda 3 \leq$960 nm) are found from (1) in FIG. 13 to be both 3.1 brix. Hence, conditions for the extent of wavelength variations in which the sugar content can be measured at an error within plus-minus 0.5 brix can be determined from the following proportional calculation.

$1\ nm{:}Xnm=(2.5+3.1+3.1\ brix){:}0.5\ brix.$

Therefore, $X=0.5\ brix/(2.5+3.1+3.1\ brix)=0.057$ is found, thus the apparatus can have the measurement reproducibility (measurable at an error within plus-minus 0.5 brix) as long as the standard deviations $\Delta\lambda 1$, $\Delta\lambda 2$ and $\Delta\lambda 3$ of the fluctuations of wavelengths (wavelength variations) are each 0.057 nm or smaller.

Next, in respect of a non-destructive sugar content measuring apparatus in which the wavelengths $\lambda 1$, $\lambda 2$ and $\lambda 3$ of laser beams fall in narrower ranges than those in the above non-destructive sugar content measuring apparatus, i.e., a non-destructive sugar content measuring apparatus in the wavelengths are selected from within the ranges of:

860 nm≦wavelength λ1≦890 nm, 900 nm≦wavelength λ2≦915 nm, 920 nm≦wavelength λ3≦940 nm, the following conditions come out.

That is, when the wavelengths vary in an extent of 1 nm, the maximum value of sugar content variations in the case of the wavelength λ1 (860 nm≦wavelength λ1≦890 nm) is found from (1) in FIG. 13 to be 1.7 brix, and also the maximum values of sugar content variations in the cases of the wavelength λ2 (900 nm≦wavelength λ2≦915 nm) and wavelength λ3 (920 nm≦wavelength λ3≦940 nm) are found from (1) in FIG. 13 to be 3.0 brix and 3.1 brix, respectively. Hence, conditions for the extent of wavelength variations in which the sugar content can be measured at an error within plus-minus 0.5 brix can be determined from the following proportional calculation.

1 $nm:Xnm=(1.7+3.0+3.1\ brix):0.5\ brix$.

Therefore, $X=0.5\ brix/(1.7+3.0+3.1\ brix)=0.064$ is found, thus the apparatus can have the measurement reproducibility (measurement at an error within plus-minus 0.5 brix) as long as the standard deviations $\Delta\lambda1$, $\Delta\lambda2$ and $\Delta\lambda3$ of the fluctuations of wavelengths (wavelength variations) are each 0.064 nm or smaller.

In a non-destructive sugar content measuring apparatus in which the wavelengths λ1, λ2 and λ3 of laser beams applied have been specified (i.e., wavelength λ1=880 nm, wavelength λ2=910 nm, wavelength λ3=930 nm), the following conditions come out.

That is, when the wavelengths vary in an extent of 1 nm, the value of sugar content variations in the case of the wavelength λ1=880 nm is found from (1) in FIG. 13 to be 1.3 brix, and also the values of sugar content variations in the cases of the wavelength λ2=910 and wavelength λ3=930 nm are found from (1) in FIG. 13 to be 2.8 brix and 2.8 brix, respectively. Hence, conditions for the extent of wavelength variations in which the sugar content can be measured at an error within plus-minus 0.5 brix can be determined from the following proportional calculation.

1 $nm:Xnm=(1.3+2.8+2.8\ brix):0.5\ brix$.

Therefore, $X=0.5\ brix/(1.3+2.8+2.8\ brix)=0.072$ is found, thus the apparatus can have the measurement reproducibility (measurement at an error within plus-minus 0.5 brix) as long as the standard deviations $\Delta\lambda1$, $\Delta\lambda2$ and $\Delta\lambda3$ of the fluctuations of wavelengths (wavelength variations) are each 0.072 nm or smaller.

Incidentally, with regard to the standard deviations $\Delta\lambda1$, $\Delta\lambda2$ and $\Delta\lambda3$ in these non-destructive sugar content measuring apparatus, the maximum values of sugar content variations in the respective wavelength regions are found on the basis of the FIG. 13 graph (sugar content variation curves) in the manner as described above and the conditions under which the sugar content can be measured at an error within plus-minus 0.5 brix are determined from the sum of such maximum values. However, depending on what wavelengths are selected for laser beams, there can be a non-destructive sugar content measuring apparatus for which it is unnecessary to determine the conditions for standard deviations $\Delta\lambda1$, $\Delta\lambda2$ and $\Delta\lambda3$ from the maximum values of sugar content variations in respect of all the three wavelengths.

The conditions under which the sugar content can be measured at an error within plus-minus 0.5 which are determined on the basis of the FIG. 13 graph (sugar content variation curves) are described below, inclusive of those for the non-destructive sugar content measuring apparatus for which it is unnecessary to determine the conditions for standard deviations $\Delta\lambda1$, $\Delta\lambda2$ and $\Delta\lambda3$ from the maximum values of sugar content variations.

That is, in respect of the non-destructive sugar content measuring apparatus in which the wavelengths λ1, λ2 and λ3 of laser beams are selected from within the ranges of:

860 nm≦wavelength λ1<900 nm, 900 nm≦wavelength λ2≦920 nm, 920 nm<wavelength λ3≦960 nm, the conditions under which the sugar content can be measured at an error within plus-minus 0.5 are determined on the basis of the FIG. 13 graph (sugar content variation curves) according to the following mathematical expression (1):

$$[f1(\lambda1)\times\Delta\lambda1+f2(\lambda2)\times\Delta\lambda2+f3(\lambda3)\times\Delta\lambda3]<0.5\ brix \quad (1)$$

In the above mathematical expression (1), $\Delta\lambda1$, $\Delta\lambda2$ and $\Delta\lambda3$ n represent standard deviations of fluctuations (wavelength variations) in the wavelengths λ1, λ2 and λ3 of the laser beams applied, and f1(λ1), f2(λ2) and f3(λ3) respectively represent sugar content variation functions (brix/nm) determined from sugar content variation curves showing the relationship between the fluctuations (wavelength variations) in the wavelengths λ1, λ2 and λ3 and the sugar content variations that accompany the former.

Here, the above sugar content variation functions f1(λ1), f2(λ2) and f3(λ3) can be determined by polynominal expansion the FIG. 13 graph (sugar content variation curves).

For example, in the FIG. 13 graph (sugar content variation curves), the following mathematical expressions can be given by polynominal expansion in the sugar content variation curve (1) where the wavelengths have varied in an extent of 1 nm.

$f1(\lambda1)=-20182.34+69.83868\times(\lambda1)-0.08055962\times(\lambda1)^2+3.097853\times10^{-5}\times(\lambda1)^3$, $f2(\lambda2)=151409.7-499.542\times(\lambda2)+0.5493413\times(\lambda2)^2-2.013521\times10^{-4}\times(\lambda2)^3$, $f3(\lambda3)=8990.066-28.1535\times(\lambda3)+0.02940324\times(\lambda3)^2-1.023846\times10^{-5}\times(\lambda3)^3$, which are premised on the non-destructive sugar content measuring apparatus in which the wavelengths λ1, λ2 and λ3 of laser beams are selected from within the ranges of:

860 nm≦wavelength λ1<900 nm, 900 nm≦wavelength λ2≦920 nm, 920 nm<wavelength λ3≦960 nm.

Then, taking the case in which the wavelengths λ1 and λ3 laser beams applied are λ1=880 nm and λ3=930 nm with standard deviations $\Delta\lambda1=0.1$ nm and $\Delta\lambda3=0.1$ nm, respectively (which means that light sources for wavelengths λ1 and λ3 are low-priced light sources having a large fluctuation of wavelength), the standard deviation $\Delta\lambda2$ in wavelength λ2 (λ2=905 nm) is found from the mathematical expression (1) to be standard deviation $\Delta\lambda2<0.033$ nm.

In the case in which the wavelength λ2 and λ3 of laser beams applied are λ2=905 nm and λ3=930 nm with standard deviations $\Delta\lambda 2=0.05$ nm and $\Delta\lambda 3=0.05$ nm, respectively, the standard deviation $\Delta\lambda 1$ in wavelength $\lambda 1$ ($\lambda 1=880$ nm) is found from the mathematical expression (1) to be standard deviation $\Delta\lambda 1<0.17$ nm (i.e., which means that a light source for wavelength $\lambda 1$ is a low-priced light sources having a large fluctuation of wavelength).

Thus, in respect of one or two light source(s) to be incorporated in the non-destructive sugar content measuring apparatus which can measure the sugar content at an error within plus-minus 0.5 brix whenever measured, light sources having a large fluctuation of wavelength may be used, and hence some cost reduction can be achieved in the manufacture of the non-destructive sugar content measuring apparatus of this type.

Incidentally, in this example, the sugar content variation curve (1) is expressed by a polynominal of degree three, but may be expressed in a polynominal of higher degree and, if possible, may be expressed by a polynominal of degree two, any of which may arbitrarily be used.

As stated previously, it may also be understood from FIG. 13 graph that the relationship between wavelength variations and sugar content variations stands linear when the wavelength variations are at least in an extent within the range of from 0.1 nm to 1 nm. Hence, with regard to the wavelength variation functions $f1(\lambda 1)$, $f2(\lambda 2)$ and $f3(\lambda 3)$, their mathematical expression may be given by polynominal expansion in the sugar content variation curve (2) where the wavelengths have varied in an extent of 0.5 nm, or may be given by polynominal expansion in the sugar content variation curve (3) where the wavelengths have varied in an extent of 0.2 nm, any of which may arbitrarily be used.

Figure 17:
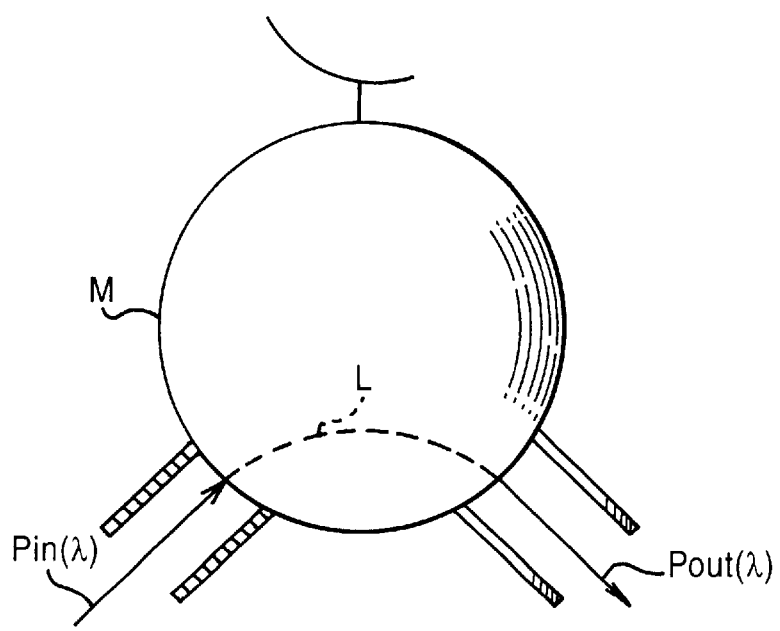
FIG. 17 illustrates the principle of a non-destructive sugar content measuring method.
Figure 18:
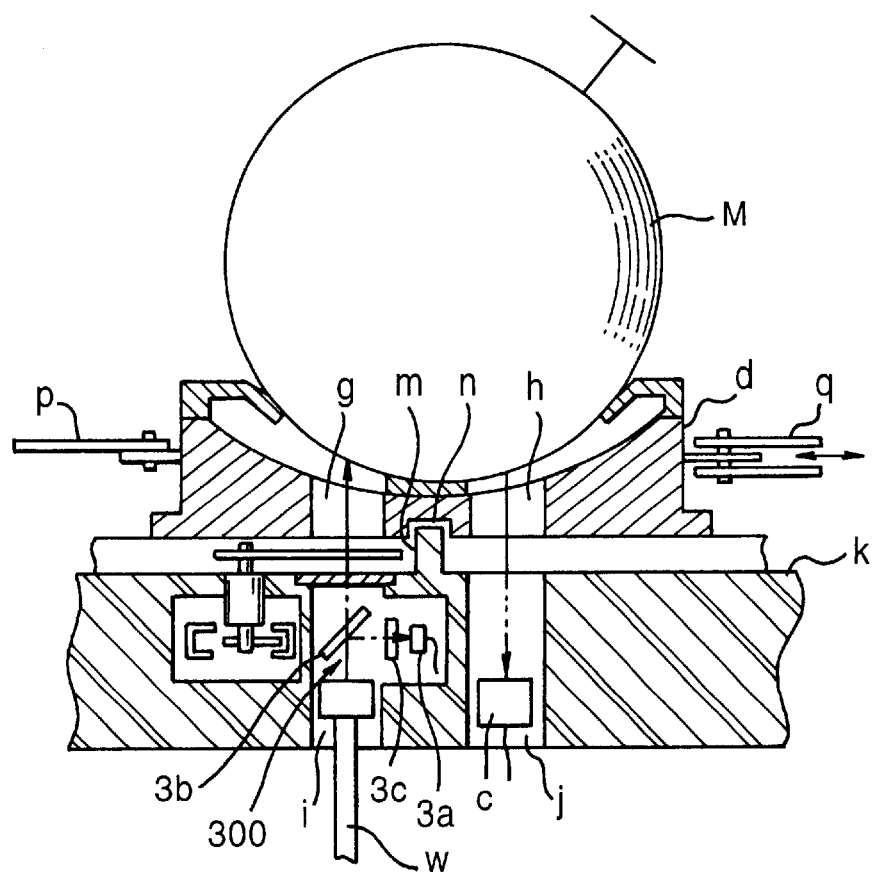
FIG. 18 is a cross-sectional illustration of the positional relation between a measuring section and a tray delivered onto the measuring section in a conventional non-destructive sugar content measuring apparatus.

Now, in the non-destructive sugar content measuring apparatus having been described above, with regard to the two wavelengths ($\lambda 1$ and $\lambda 3$) other than the wavelength $\lambda 2$ (900 nm $\leq$ wavelength $\lambda 2 \leq$ 920 nm) where the sugar absorbs light, they are used to correct optical path length (see L in FIG. 17) necessary for the analysis made in the transmission method (which is a system in which as shown in FIG. 17 a laser beam is made incident on the fruit M at its light incident portion and the laser beam having transmitted through the interior of the fruit M is detected at a light emergent portion set at a position different from the light incident portion, and is distinguished from the reflection method in which the light incident portion and the light emergent portion are set at the same position). The sugar content of vegetables and fruits is determined by employing the multiple regression analysis, which is as described above.

In this case, in the above non-destructive sugar content measuring apparatus, the wavelength regions of the two wavelengths ($\lambda 1$ and $\lambda 3$) are set at both sides of the wavelength $\lambda 2$ (900 nm $\leq$ wavelength $\lambda 2 \leq$ 920 nm) positioned at the middle. Alternatively, these two wavelengths may be set on the side of a shorter wavelength than the wavelength where the sugar absorbs light.

More specifically, the non-destructive sugar content measuring apparatus may be set up by setting the wavelengths $\lambda 1$, $\lambda 2$ and $\lambda 3$ of the laser beams to be within the ranges of:

800 nm $\leq$ wavelengths $\lambda 1$, $\lambda 2 < 900$ nm, 900 nm $\leq$ wavelength $\lambda 3 \leq 920$ nm, (provided that the wavelengths $\lambda 1$ and $\lambda 2$ have a wavelength distance between them of 10 nm or larger). When this non-destructive sugar content measuring apparatus is compared with the non-destructive sugar content measuring apparatus having been described previously, the coefficients A, B and C of the aforesaid Equation (4) differ from each other as a matter of course, but the both are identical as the principle of non-destructive sugar content measurement made by the transmission method. Thus, this non-destructive sugar content measuring apparatus can also be made to have the measurement reproducibility (i.e., measurable at an error within plus-minus 0.5 brix) on the basis of the like ideas.

Figure 14:
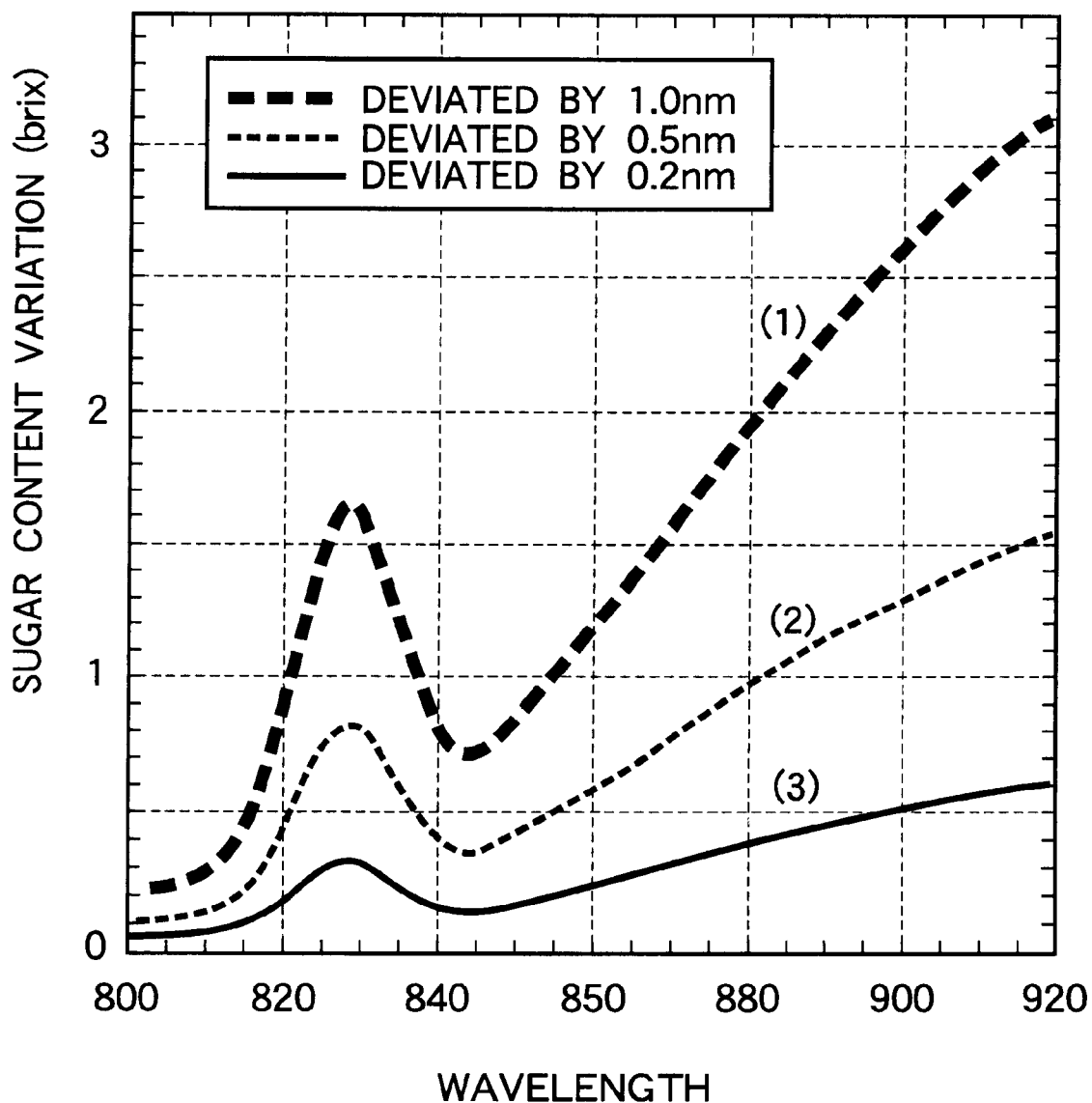
FIG. 14 is a graph showing sugar content variation curves where only one wavelength has been (1) deviated by 1 nm, (2) deviated by 0.5 nm and (3) deviated by 0.2 nm, among three wavelengths used in the non-destructive sugar content measuring apparatus in which the wavelengths $\lambda 1$, $\lambda 2$ and $\lambda 3$ of laser beams are selected from within the ranges of from 800 nm$\leq$wavelengths $\lambda 1$ and $\lambda 2$<900 nm, and 900 nm$\leq$wavelength $\lambda 3 \leq$920 nm (provided that the wavelengths $\lambda 1$ and $\lambda 2$ have a wavelength distance between them of 10 nm or larger).

Accordingly, premised on a non-destructive sugar content measuring apparatus in which the wavelengths $\lambda 1$, $\lambda 2$ and $\lambda 3$ of laser beams are selected from within the ranges of:

800 nm $\leq$ wavelengths $\lambda 1$, $\lambda 2 < 900$ nm, 900 nm $\leq$ wavelength $\lambda 3 \leq 920$ nm, (provided that the wavelengths $\lambda 1$ and $\lambda 2$ have a wavelength distance between them of 10 nm or larger); a titanium-sapphire laser was used as a laser light source, and a laser beam emitted from the laser light source was made incident on a fruit (muskmelon), varying the wavelengths of the laser beam, to determine what percent (%) its transmittance varies and also to determine, according to Equations (2) and (4) set forth previously, sugar content variations caused when the transmittance varies, where the results shown in FIG. 14 were obtained. Incidentally, it has been confirmed from the graph in FIG. 14 that the relationship between wavelength variations and sugar content variations stands linear when the wavelength variations are at least in an extent within the range of from 0.1 nm to 1 nm.

Accordingly, in respect of the non-destructive sugar content measuring apparatus in which the wavelengths $\lambda 1$, $\lambda 2$ and $\lambda 3$ of laser beams are selected from within the ranges of:

800 nm $\leq$ wavelengths $\lambda 1$, $\lambda 2 < 900$ nm, 900 nm $\leq$ wavelength $\lambda 3 \leq 920$ nm, (provided that the wavelengths $\lambda 1$ and $\lambda 2$ have a wavelength distance between them of 10 nm or larger); maximum values of sugar content variations in the respective wavelength regions are found on the basis of the FIG. 14 graph, and the extent of wavelength variations in which the sugar content can be measured at an error within plus-minus 0.5 brix is determined from the sum of such maximum values.

More specifically, when the wavelengths vary in an extent of 1 nm, the maximum values of sugar content variations in the case of the wavelengths $\lambda 1$ and $\lambda 2$ (800 nm $\leq$ wavelengths $\lambda 1$, $\lambda 2 < 900$ nm) are found from (1) in FIG. 14 to be both 2.6 brix, and also the maximum value of sugar content variations in the case of the wavelength $\lambda 3$ (900 nm < wavelength $\lambda 3 \leq 920$ nm) is found from (1) in FIG. 14 to be 3.1 brix. Hence, conditions for the extent of wavelength variations in which the sugar content can be measured at an error within plus-minus 0.5 brix can be determined from the following proportional calculation.

1 $nm:Xnm=(2.6+2.6+3.1\ brix):0.5\ brix$.

Therefore, $X=0.5\text{brix}/(2.6+2.6+3.1\text{brix})=0.060$ is found, thus the apparatus can have the measurement reproducibility (measurable at an error within plus-minus 0.5 brix) as long as the standard deviations $\Delta\lambda 1$, $\Delta\lambda 2$ and $\Delta\lambda 3$ of the fluctuations of wavelengths (wavelength variations) are each 0.060 nm or smaller.

Incidentally, the reason why the standard deviations of this non-destructive sugar content measuring apparatus ($\Delta\lambda 1$, $\Delta\lambda 2$ and $\Delta\lambda 3=0.060$) is greater than the standard deviations of the non-destructive sugar content measuring apparatus described previously ($\Delta\lambda 1$, $\Delta\lambda 2$ and $\Delta\lambda 3=0.057$)

in which the wavelength regions of the two wavelengths ($\lambda 1$ and $\lambda 3$) are set at both sides of the wavelength $\lambda 2$ (900 nm≤wavelength $\lambda 2$≤920 nm) positioned at the middle is that, with regard to the two wavelengths other than the wavelength where the sugar absorbs light, the light having a shorter wavelength is less affected by water.

In other words, when the above two wavelengths are selected, they may be selected from a region of shorter wavelength than the wavelength where the sugar absorbs light. This may rather bring about an advantage that the latitude for the fluctuation of wavelength in the laser beam can be made broader.

With regard to the standard deviations $\Delta\lambda 1$, $\Delta\lambda 2$ and $\Delta\lambda 3$ in this non-destructive sugar content measuring apparatus, the maximum values of sugar content variations in the respective wavelength regions are also found on the basis of the FIG. 14 graph (sugar content variation curves) in the manner as described above and the conditions under which the sugar content can be measured at an error within plus-minus 0.5 brix are determined from the sum of such maximum values. However, depending on what wavelengths are selected for laser beams, there can be a non-destructive sugar content measuring apparatus for which it is unnecessary to determine the conditions for standard deviations $\Delta\lambda 1$, $\Delta\lambda 2$ and $\Delta\lambda 3$ from the maximum values of sugar content variations in respect of all the three wavelengths.

The conditions under which the sugar content can be measured at an error within plus-minus 0.5 which are determined on the basis of the FIG. 14 graph (sugar content variation curves) are described below, inclusive of those for the non-destructive sugar content measuring apparatus for which it is unnecessary to determine the conditions for standard deviations $\Delta\lambda 1$, $\Delta\lambda 2$ and $\Delta\lambda 3$ from the maximum values of sugar content variations.

That is, in respect of the non-destructive sugar content measuring apparatus in which the wavelengths $\lambda 1$, $\lambda 2$ and $\lambda 3$ of laser beams are selected from within the ranges of:

800 nm≤wavelengths $\lambda 1$, $\lambda 2$<900 nm, 900 nm≤wavelength $\lambda 3$≤920 nm, the conditions under which the sugar content can be measured at an error within plus-minus 0.5 are determined on the basis of the FIG. 14 graph (sugar content variation curves) according to the following mathematical expression (1):

$$[f1(\lambda 1)\times\Delta\lambda 1 + f2(\lambda 2)\times\Delta\lambda 2 + f3(\lambda 3)\times\Delta\lambda 3] < 0.5 \text{ brix} \quad (1)$$

In the above mathematical expression (1), $\Delta\lambda 1$, $\Delta\lambda 2$ and $\Delta\lambda 3$ represent standard deviations of fluctuations (wavelength variations) in the wavelengths $\lambda 1$, $\lambda 2$ and $\lambda 3$ of laser beams applied, and $f1(\lambda 1)$, $f2(\lambda 2)$ and $f3(\lambda 3)$ respectively represent sugar content variation functions (brix/nm) determined from sugar content variation curves showing the relationship between the fluctuations (wavelength variations) in the wavelengths $\lambda 1$, $\lambda 2$ and $\lambda 3$ and the sugar content variations that accompany the former.

Here, the above sugar content variation functions $f1(\lambda 1)$, $f2(\lambda 2)$ and $f3(\lambda 3)$ can be determined by polynominal expansion in the FIG. 14 graph (sugar content variation curves).

For example, in the FIG. 14 graph (sugar content variation curves), the following mathematical expression can be given by polynominal expansion in the sugar content variation curve (1) where the wavelengths have varied in an extent of 1 nm.

In the case of 800 nm≤wavelengths $\lambda 1$, $\lambda$.820 nm, $$f(\lambda) = -74458.74 + 277.6852\times\lambda - 0.345206\times\lambda^2 + 1.43052\times10^{-4}\times\lambda^3,$$

In the case of 820 nm<wavelengths $\lambda 1$, $\lambda 2$≤840 nm, $$f(\lambda) = -270722.5 + 972.2863\times\lambda - 1.163856\times\lambda^2 + 4.643458\times10^{-4}\times\lambda^3,$$

In the case of 840 nm<wavelengths $\lambda 1$, $\lambda 2$, $\lambda 3$≤920 nm, $$f(\lambda) = 8564.296 - 29.36077\times\lambda + 0.033502\times\lambda^2 - 1.272059\times10^{-6}\times\lambda^3,$$

which are premised on the non-destructive sugar content measuring apparatus in which the wavelengths $\lambda 1$, $\lambda 2$ and $\lambda 3$ of laser beams are selected from within the ranges of:

800 nm≤wavelengths $\lambda 1$, $\lambda 2$<900 nm, 900 nm≤wavelength $\lambda 3$≤920 nm.

Then, taking the case in which the wavelengths $\lambda 1$ and $\lambda 2$ of laser beams applied are $\lambda 1=840$ nm and $\lambda 2=880$ nm with standard deviations $\Delta\lambda 1=0.1$ nm and $\Delta\lambda 2=0.1$ nm, respectively (which means that light sources for wavelengths $\lambda 1$ and $\lambda 2$ are low-priced light sources having a large fluctuation of wavelength), the standard deviation $\Delta\lambda 3$ in wavelength $\lambda 3$ ($\lambda 3=905$ nm) is found from the mathematical expression (1) to be standard deviation $\Delta\lambda 3<0.09$ nm.

In the case in which the wavelength $\lambda 2$ and $\lambda 3$ of laser beams applied are $\lambda 2=880$ nm and $\lambda 3=905$ nm with standard deviations $\Delta\lambda 2=0.05$ nm and $\Delta\lambda 3=0.05$ nm, respectively, the standard deviation $\Delta\lambda 1$ in wavelength $\lambda 1$ ($\lambda 1=840$ nm) is found from the mathematical expression (1) to be standard deviation $\Delta\lambda 1<0.33$ nm (i.e., which means that a light source for wavelength $\lambda 1$ is a low-priced light sources having a large fluctuation of wavelength).

Thus, in respect of one or two light source(s) to be incorporated in the non-destructive sugar content measuring apparatus which can measure the sugar content at an error within plus-minus 0.5 brix whenever measured, light sources having a large fluctuation of wavelength may be used, and hence some cost reduction can be achieved in the manufacture of the non-destructive sugar content measuring apparatus of this type.

Incidentally, in this example, too, the sugar content variation curve (1) is expressed by a polynominal of degree three, but may be expressed in a polynominal of higher degree and, if possible, may be expressed by a polynominal of degree two, any of which may arbitrarily be used.

It may also be understood from FIG. 14 graph that the relationship between wavelength variations and sugar content variations stands linear when the wavelength variations are at least in an extent within the range of from 0.1 nm to 1 nm. Hence, with regard to the wavelength variation functions $f1(\lambda 1)$, $f2(\lambda 2)$ and $f3(\lambda 3)$, their mathematical expression may be given by polynominal expansion in the sugar content variation curve (2) where the wavelengths have varied in an extent of 0.5 nm, or may be given by polynominal expansion in the sugar content variation curve (3) where the wavelengths have varied in an extent of 0.2 nm, any of which may arbitrarily be used.

Now, as factors which may cause the fluctuations of wavelengths in laser beams, there are characteristics of laser light sources themselves to be used, characteristics of their power sources themselves, surroundings in which the laser light sources are installed (i.e., for example, whether or not there is a vibration source in the vicinity of installation place, and whether or not any means is taken so as for the vibration, if any, not to come to the laser light sources), the presence of any return light to laser light sources which may impair their oscillation intensity, and so forth. Methods by which these factors are eliminated so that the standard deviations $\Delta\lambda 1$, $\Delta\lambda 2$ and $\Delta\lambda 3$ of wavelength variations can be kept small in the wavelengths λ1, λ2 and λ3 are exemplified by the following methods.

One is, e.g., a method in which semiconductor lasers having been made vertically single-mode by means of a diffraction grating are used as light sources of laser beams.

Such semiconductor lasers having been made vertically single-mode by means of a diffraction grating can make wavelengths lock to make the wavelengths less fluctuate to become stable. Hence, with regard to the standard deviations Δλ1, Δλ2 and Δλ3 of wavelength variations in the wavelengths λ1, λ2 and λ3, they can be controlled to, e.g., the values of 0.057 nm to 0.072 nm or smaller stated previously.

Such semiconductor lasers may include DBR (distributed Bragg reflector) lasers, DFB (distributed feedback) lasers and fiber grating lasers.

As methods for avoiding the presence of any return light to laser light sources which may impair their oscillation intensity, exemplified is a method in which the laser beams having wavelengths λ1, λ2 and λ3 are respectively made incident on vegetables and fruits through optical fibers and the optical fibers are kept obliquely cut at their ends on the laser beam incident side.

According to this method, the optical fibers are kept obliquely cut at their ends on the laser beam incident side. Hence, when the laser beams emitted from laser light sources enter the optical fibers, the reflection of laser beams which occurs at the optical fiber ends on the laser beam incident side is no longer backward directed to the laser light sources, so that the oscillation intensity of each laser light source can be made stable. In addition, in the case when the laser light sources are vertical multimode oscillation type semiconductor lasers, the wavelengths may less fluctuate because the reflected light does not return to the laser light sources, so that, with regard to the standard deviations Δλ1, Δλ2 and Δλ3 of wavelength variations in the wavelengths λ1, λ2 and λ3, they can be controlled to, e.g., the above values of 0.057 nm to 0.072 nm or smaller.

As another method for controlling the standard deviations Δλ1, Δλ2 and Δλ3 to make them smaller, also exemplified is a method in which the laser beam light sources are made up using the semiconductor lasers having been made vertically single-mode or the vertical multimode oscillation type semiconductor lasers and also their power sources are made up using constant-current power sources having a current stability of 0.1 mA.

According to this method, the light sources can be made to have a stable intensity because the constant-current power sources having a current stability of 0.1 mA are used as power sources, and in addition the wavelengths may less fluctuate when the laser light sources are the vertical multimode oscillation type semiconductor lasers. Hence, with regard to the standard deviations Δλ1, Δλ2 and Δλ3 of wavelength variations in the wavelengths λ1, λ2 and λ3, they can be controlled to, e.g., the above values of 0.057 nm to 0.072 nm or smaller.

Figure 15:
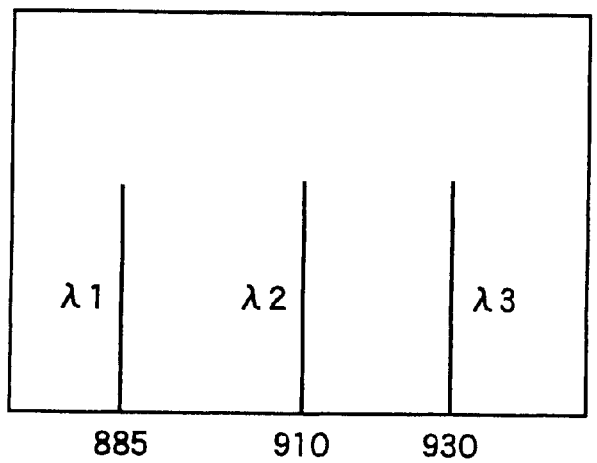
FIG. 15 shows an oscillation spectrum of three semiconductor lasers in vertical multimode oscillation.
Figure 16:
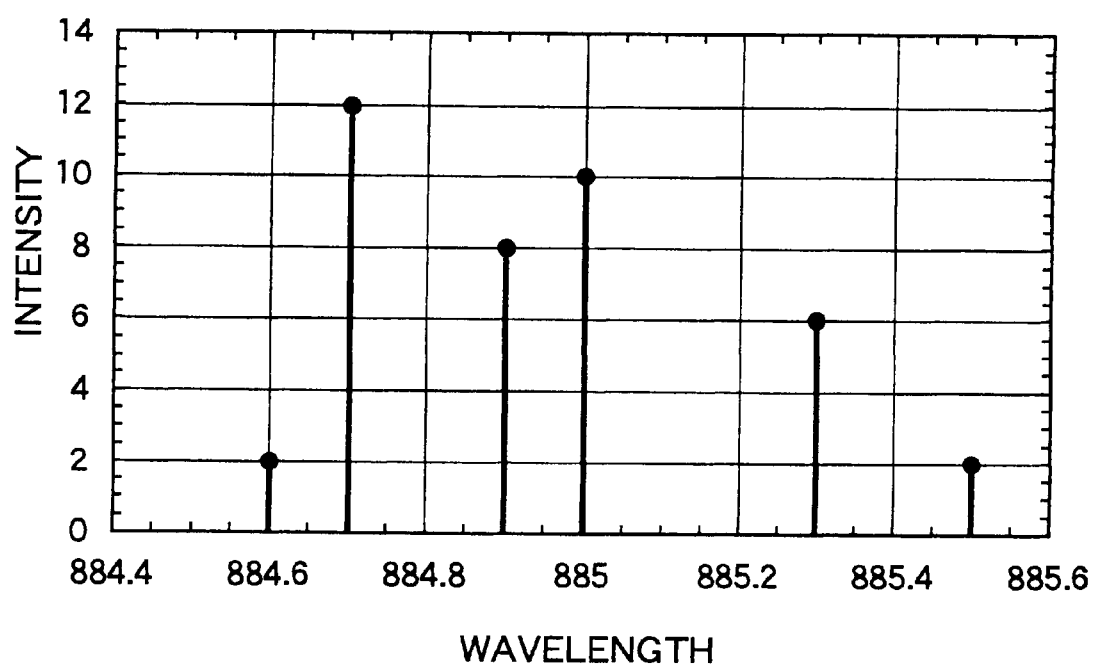
FIG. 16 is an enlarged view of the oscillation spectrum of a semiconductor laser in vertical multimode oscillation.

Here, the wavelengths in the vertical multimode oscillation type semiconductor lasers are defined in the following way. First, the oscillation spectrum of a semiconductor laser in vertical multimode oscillation, when viewed in a broad wavelength region, looks as if oscillations each take place at one wavelength as shown in FIG. 15. However, in an enlarged view of one oscillation spectrum in FIG. 15 (e.g., wavelength λ1), such oscillation takes place actually at many wavelengths as shown in FIG. 16 (I=1 to 6).

Now, the wavelengths of the semiconductor laser in such vertical multimode oscillation are commonly often defined in terms of the central wavelength. However, in the case when laser beams are made incident on vegetables and fruits to determine their absorbance and the sugar content is obtained from such absorbance as in the non-destructive sugar content measuring apparatus according to the present invention, the central wavelength can not simply be used because the absorption of light in the water constituting the background has a wavelength dependence. This is because, even when the central wavelength is as it is, the water may have influence at a degree which differs depending on changes in shape of oscillation spectra.

Accordingly, in the present invention, the wavelength dependence of the absorption of light by water is taken into account, and a weighted mean of oscillation spectra which is obtained using the absorbance of water is defined as the wavelength of the semiconductor laser in vertical multimode oscillation.

More specifically, where the wavelengths of laser beams are represented by λiI (i=1 to 3, I=an integer of 1 to N), the absorbance of water at those wavelengths by αiI (α=1 to 3, I=an integer of 1 to N), and the intensity by AiI (i=1 to 3, I=an integer of 1 to N), the weighted mean is given as:

$$\lambda i=(\Sigma AiI\times\alpha iI\times\lambda iI)/(\Sigma AiI\times\alpha iI).$$

The absorbance of water in the range of from 800 nm to 960 nm is shown below.

First, that of from 800 nm to 860 nm is expressed by the following equation:

$$\alpha=M0+M1\times\lambda+M2\times\lambda^2+M3\times\lambda^3+M4\times\lambda^4+M5\times\lambda^5,$$

wherein;

M0=2258.8755,

M1=−9.1762122,

M2=0.011818366,

M3=−2.3097722×10$^{-6}$,

M4=−5.5040023×10$^{-9}$.

M5=2.9175349×10$^{-12.}$

That of from 860 nm to 960 nm is expressed by the following equation:

$$\alpha=M0+M1\times\lambda+M2\times\lambda^2+M3\times\lambda^3+M4\times\lambda^4,$$

wherein;

M0=5967.629109,

M1=−27.15611592,

M2=0.04633395544,

M3=−3.513071525×10$^{-5}$,

M4=9.987384597×10$^{-9}$.

Then, according to these equations, in the case of, e.g., the semiconductor laser of vertical multimode oscillation as shown in FIG. 16, the weighted-mean wavelength λ1 can be found from the data of:

|       | (wavelength λ1I) | (intensity A1I) |
|-------|------------------|-----------------|
| I = 1 | 884.60           | 2.000           |
| I = 2 | 884.70           | 12.000          |
| I = 3 | 884.90           | 8.000           |
| I = 4 | 885.00           | 10.000          |
| I = 5 | 885.30           | 6.000           |
| I = 6 | 885.50           | 2.000           | and the absorbance of water, to be 884.94.

Thus, according to the invention of first embodiment;
the wavelengths λ1, λ2 and λ3 of the laser beams satisfy the conditions of:

860 nm≦wavelength λ1<900 nm, 900 nm≦wavelength λ2≦920 nm, 920 nm<wavelength λ3≦960 nm, and, where standard deviations of wavelength variations in the wavelengths λ1, λ2 and λ3 are represented by Δλ1, Δλ2 and Δλ3, respectively, satisfy the condition of the following mathematical expression (1); and according to the invention of second embodiment;

the wavelengths λ1, λ2 and λ3 of the laser beams satisfy the conditions of:

800 nm≦wavelengths λ1, λ2<900 nm, 900 nm≦wavelength λ3≦920 nm, the wavelengths λ1 and λ2 having a wavelength distance between them of 10 nm or larger; and, where standard deviations of wavelength variations in the wavelengths λ1, λ2 and λ3 are represented by Δλ1, Δλ2 and Δλ3, respectively, satisfy the condition of the following mathematical expression (1):

$$[f1(\lambda 1) \times \Delta\lambda 1 + f2(\lambda 2) \times \Delta\lambda 2 + f3(\lambda 3) \times \Delta\lambda 3] < 0.5 \ brix \qquad (1);$$

in which mathematical expression (1), f1(λ1), f2(λ2) and f3(λ3) respectively represent sugar content variation functions (brix/nm) determined from sugar content variation curves showing the relationship between the wavelength variations in the wavelengths λ1, λ2 and λ3 and the sugar content variations that accompany the former.

Hence, the present invention has the effect of enabling the measurement of sugar content at an error within plus-minus 0.5 brix whenever the same vegetables and fruits kept at a constant temperature are measured by means of the non-destructive sugar content measuring apparatus according to the first and second embodiments of the invention.

The present invention will be described below in greater detail by giving Examples and with reference to the accompanying drawings.

EXAMPLE 1

Figure 1:
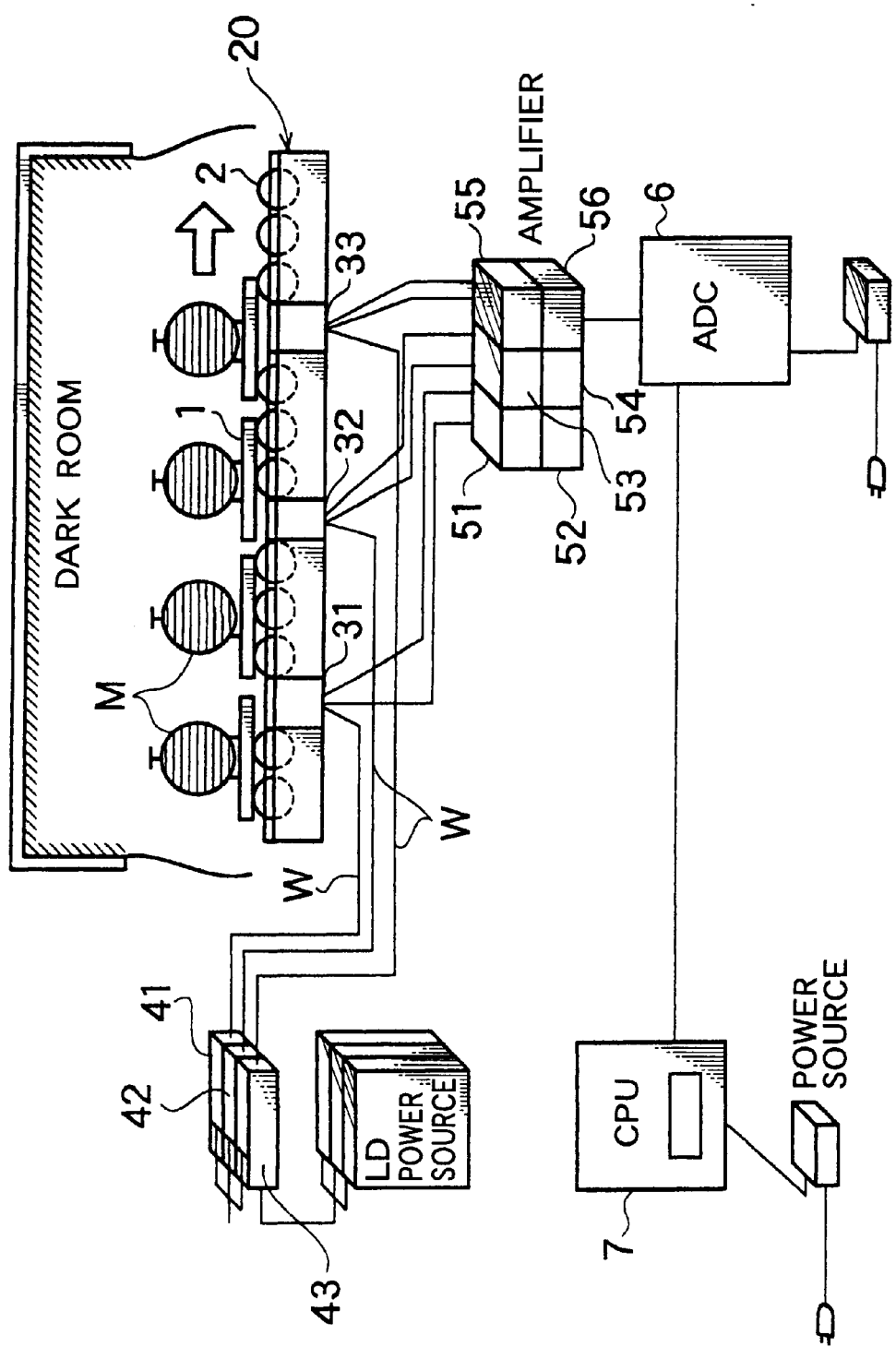
FIG. 1 is an illustration of the whole construction of a non-destructive sugar content measuring apparatus according to Example 1.
Figure 2:
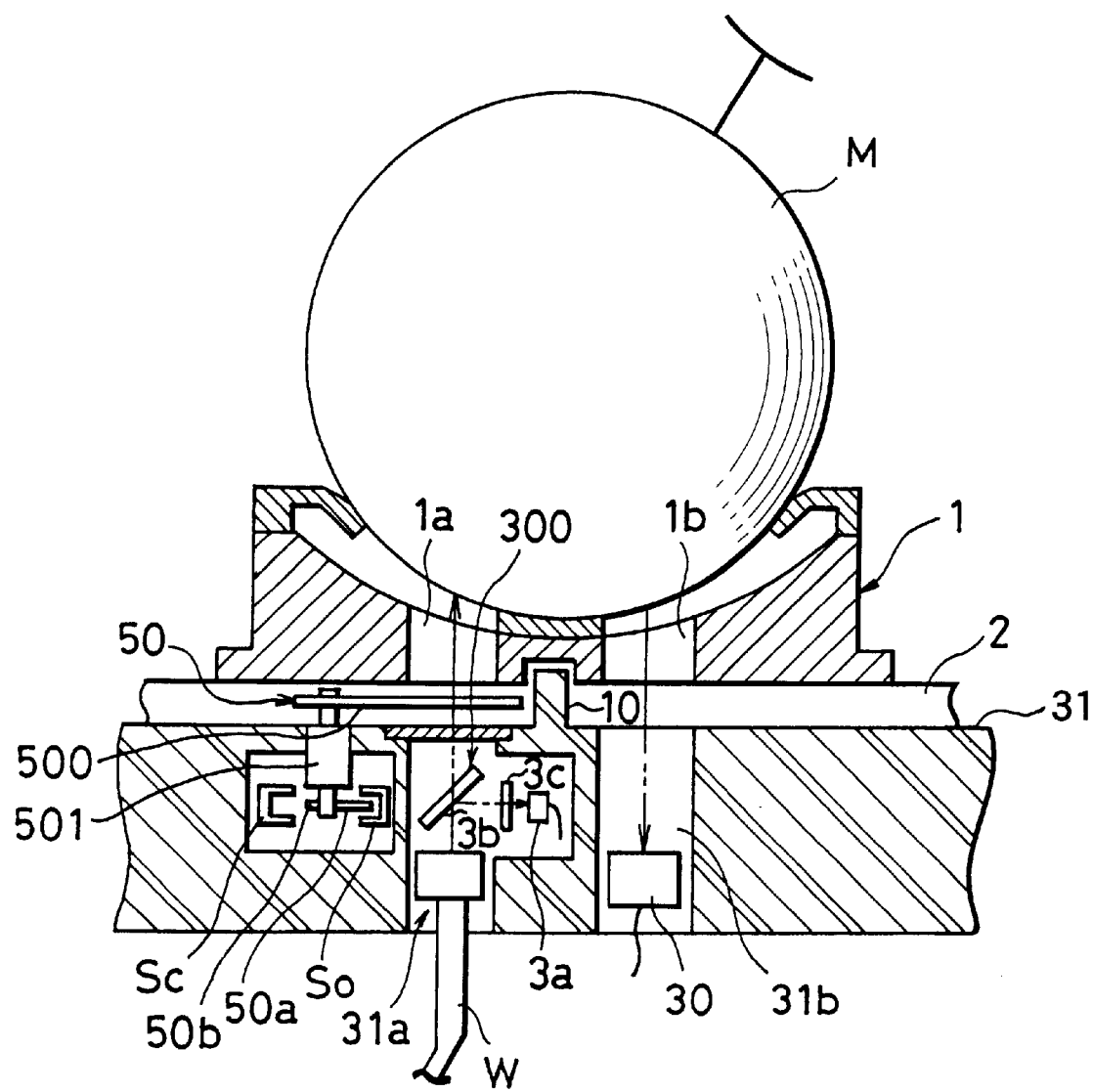
FIG. 2 is a cross-sectional illustration of the positional relation between a first measuring section and a tray delivered onto the first measuring section in the non-destructive sugar content measuring apparatus according to Example 1.

FIGS. 1 and 2 shows a non-destructive sugar content measuring apparatus according to Example 1.

More specifically, this non-destructive sugar content measuring apparatus is constituted chiefly of a transport path 20 provided in its lengthwise direction with a transport means 2 such as a roller conveyor or belt conveyor which delivers trays 1 on which vegetables and fruits M such as muskmelons are placed; a first measuring section 31, a second measuring section 32 and a third measuring section 33 which are consecutively disposed in the transport path 20 at given intervals; a first light source 41 which emits a laser beam of wavelength λ1 (λ1=880 nm) to the interior of the first measuring section 31 through an optical fiber w; a second light source 42 which emits a laser beam of wavelength λ2 (λ2=910 nm) to the interior of the second measuring section 32 through an optical fiber w; a third light source 43 which emits a laser beam of wavelength λ3 (λ3=930 nm) to the interior of the third measuring section 33 through an optical fiber w; a first distributor 3b which is provided on the leading-end side of the optical fiber w connected to the first light source 41 and distributes part of the laser beam of wavelength λ1 to guide it to an output monitoring detector 3a; a second distributor (not shown) which is provided on the leading-end side of the optical fiber w connected to the second light source 42 and distributes part of the laser beam of wavelength λ2 to guide it to another output monitoring detector outside illustration; a third distributor (not shown) which is provided on the leading-end side of the optical fiber w connected to the third light source 43 and distributes part of the laser beam of wavelength λ3 to guide it to still another output monitoring detector outside illustration; shutter means outside illustration which are respectively provided on the laser beam emergent sides in the first measuring section 31, second measuring section 32 and third measuring section 33 and are movable in accordance with sensing signals sent from vegetables and fruits sensing means (not shown) (a shutter means 50 in the first measuring section 31 is shown in FIG. 2); detectors outside illustration which are also respectively disposed in the first measuring section 31, second measuring section 32 and third measuring section 33 and measure the amount of light of the respective laser beams of wavelengths λ1, λ2 and λ3, becoming emergent from the vegetables and fruits M (a detector 30 in the first measuring section 31 is shown in FIG. 2); a first monitoring amplifier 51 and a first amplifier 52 which are connected to the output monitoring detector 3a and the detector 30 in the first measuring section 31 and amplify output signals corresponding to the amount of detected light of each laser beam of wavelength λ1, outputted from these detectors; a second monitoring amplifier 53 and a second amplifier 54 which are connected to an output monitoring detector and a detector (which are outside illustration) in the second measuring section 32 and amplify output signals corresponding to the amount of detected light of each laser beam of wavelength λ2, outputted from these detectors; a third monitoring amplifier 55 and a third amplifier 56 which are connected to an output monitoring detector and a detector (which are outside illustration) in the third measuring section 33 and amplify output signals corresponding to the amount of detected light of each laser beam of wavelength λ3, outputted from these detectors; an ADC (analog-digital converter) 6 which are connected to these amplifiers and converts their analog output signals into digital signals; and a CPU 7 which arithmetically operates the digital signals sent from this ADC 6, to calculate the sugar content of the vegetables and fruits M.

First, as the first light source 41, second light source 42 and third light source 43, DBR lasers, which are semiconductor lasers having been made vertically single-mode by means of a diffraction grating, are respectively used. Also, these light sources 41 to 43 are disposed on a table (not shown) installed via an absorption rubber which absorbs vibrations, and are so regulated that any vibrations coming about in the surroundings do not travel to the light sources 41 to 43. At the same time, support members (not shown) which support the optical fibers w are also provided with the absorption rubber between the supporting members and the optical fibers w, and are so regulated that any vibrations do not travel to the optical fibers w. Also, constant-current power sources having a current stability of 0.1 mA are connected to power sources of the first light source 41, second light source 42 and third light source 43, and the optical fibers w connected to the light sources 41 to 43 are kept obliquely cut at their ends on the laser beam incident side so that the reflection of laser beams which occurs at the optical fiber ends on the laser beam incident side may no longer be backward directed to the light sources 41 to 43.

Here, with regard to the laser beams of wavelength λ1 (λ1=880 nm), wavelength λ2 (λ2=910 nm) and wavelength λ3 (λ3=930 nm), emitted from the first light source 41, second light source 42 and third light source 43, respectively, their wavelengths were monitored with an optical-spectrum analyzer and the standard deviations $\Delta\lambda 1$, $\Delta\lambda 2$ and $\Delta\lambda 3$ of wavelength variations in the wavelengths $\lambda 1$, $\lambda 2$ and $\lambda 3$ were determined to find that they were smaller than 0.057 nm in all the wavelengths $\lambda 1$, $\lambda 2$ and $\lambda 3$.

Figure 3:
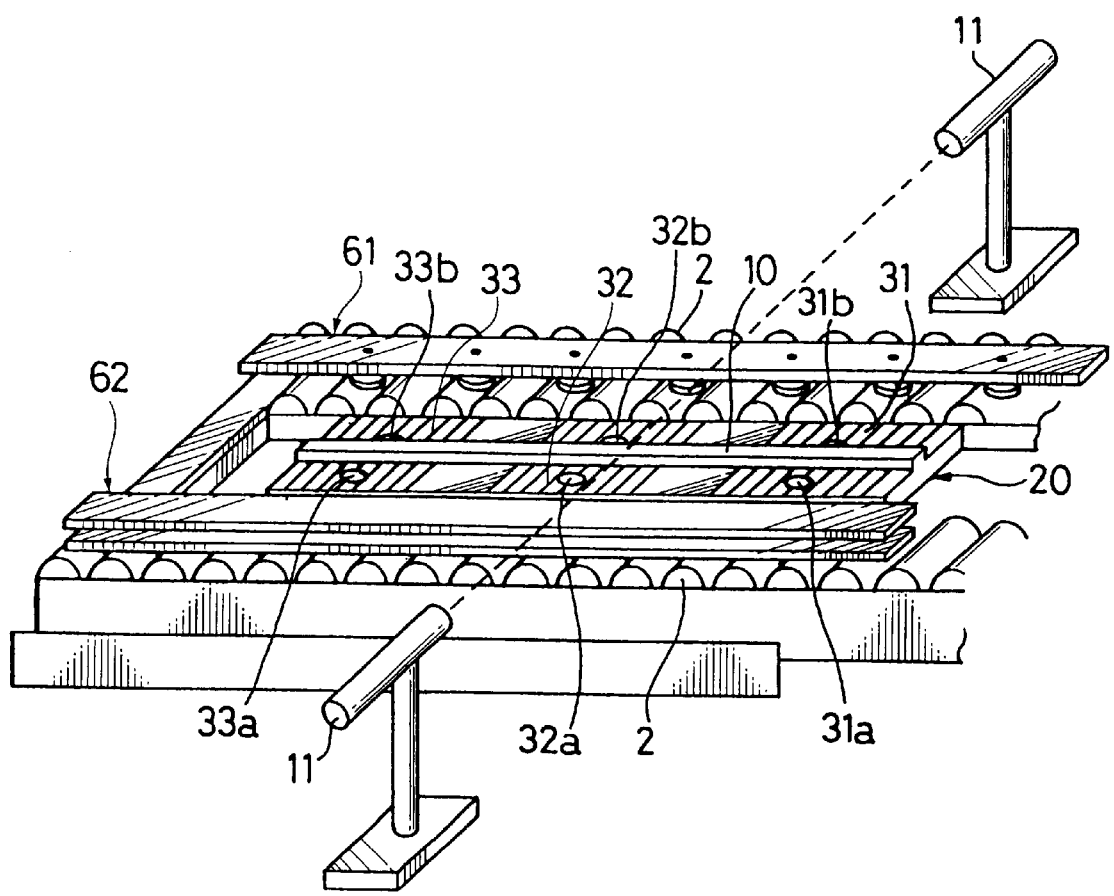
FIG. 3 is a perspective illustration of the main part of the non-destructive sugar content measuring apparatus according to Example 1.

Then, the first measuring section 31, second measuring section 32 and third measuring section 33 are, as shown in FIG. 3, consecutively disposed in the transport path 20 in its lengthwise direction and at given intervals. The measuring sections 31, 32 and 33 are provided with a linear projection 10 extending along their middle portions on the top side. Also, in the measuring sections 31, 32 and 33, measurement-section-side light passages 31a and 31b, 32a and 32b, and 33a and 33b, respectively, are provided in pairs openly on both sides of the linear projection 10 positioned at the middle, and the measuring sections are also respectively provided with the vegetables and fruits sensing means which sense the presence or absence of vegetables and fruits delivered to come to the measuring sections, and output the detected signals to the shutter means (a vegetables and fruits sensing means 11 provided in the first measuring section 31 is shown in FIG. 3).

Figure 4:
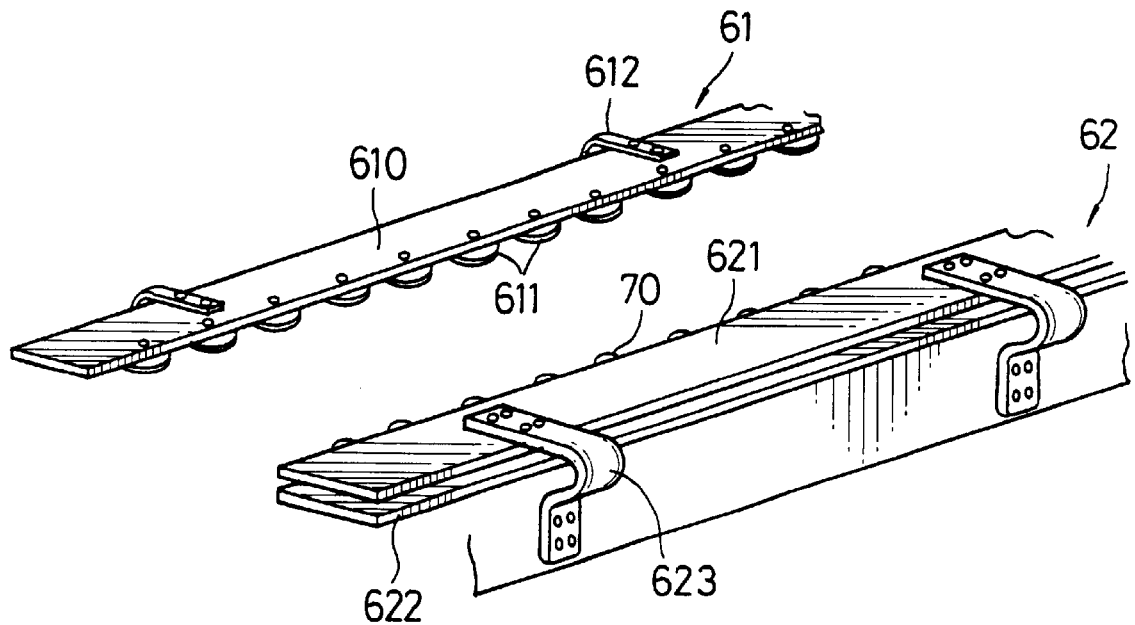
FIG. 4 is a perspective view of a tray delivery position control means used in the non-destructive sugar content measuring apparatus according to Example 1.
Figure 5:
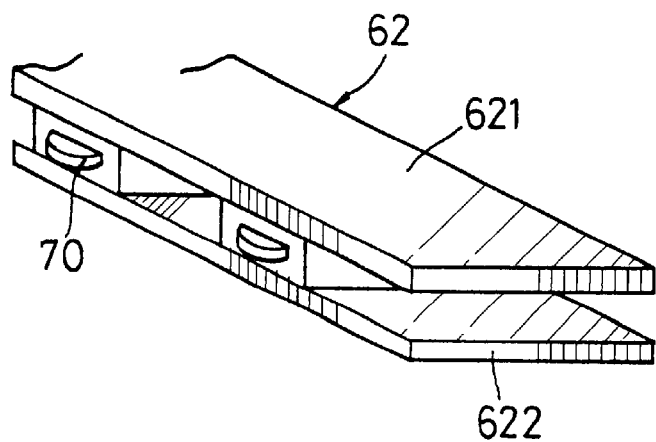
FIG. 5 is a partial perspective view of a second side bar that constitutes part of the tray delivery position control means shown in FIG. 4.

On the both sides of the transport path 20 along which the first measuring section 31, second measuring section 32 and third measuring section 33 are disposed, a first side bar 61 and a second side bar 62 which serve as a delivery position control means for controlling tray delivery position are provided as shown in FIGS. 3 to 5. Also, the second side bar 62 has a pressing means for pressing to the first side bar 61 side the tray coming to be delivered.

Figure 6:
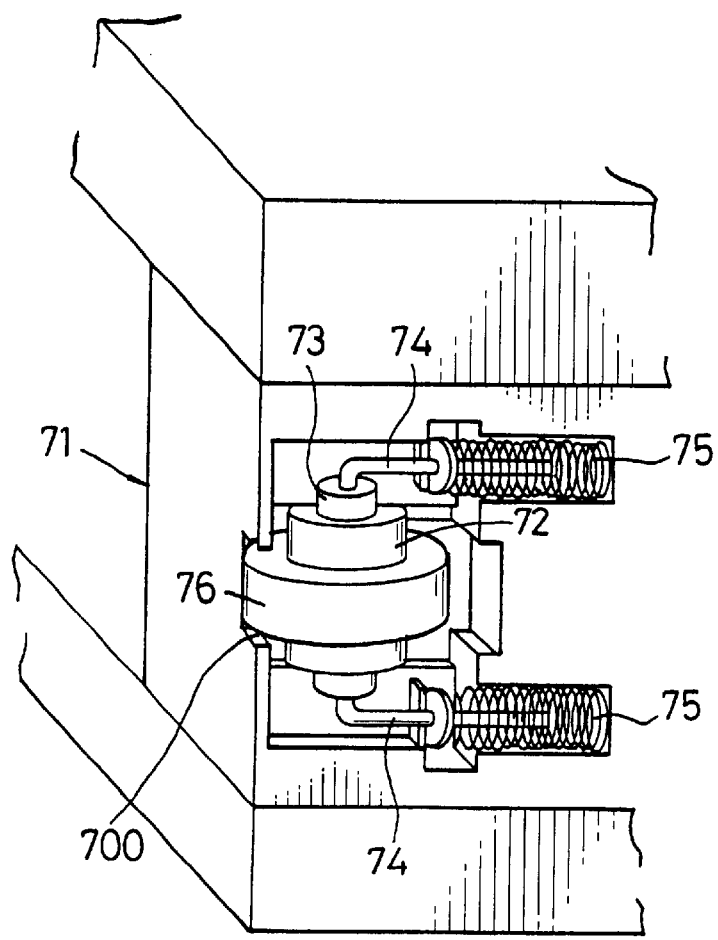
FIG. 6 is a partially broken perspective illustration of the construction of a pressing means incorporated in the second side bar shown in FIG. 5.
Figure 7:
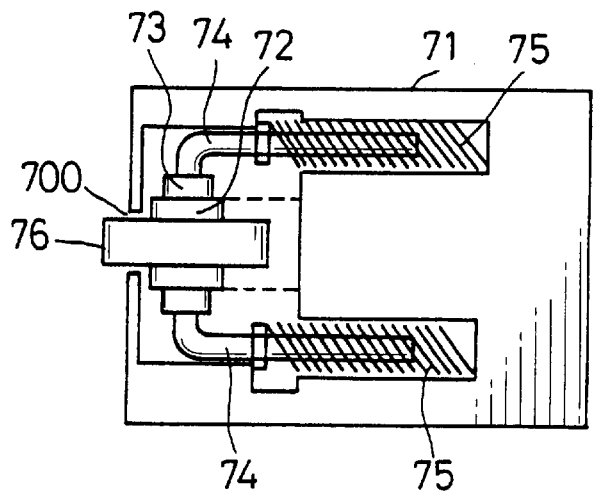
FIG. 7 is a cross-sectional view of the pressing means shown in FIG. 6.

First, the first side bar 61 is, as shown in FIG. 4, constituted of a first side bar main body 610 made of a metal such as iron, a plurality of rotary-disk rollers 611 provided to this first side bar main body 610, and a fixing member 612 that fixes the first side bar main body 610 to the one side edge of the transport path. Meanwhile, the second side bar 62 is, as shown in FIGS. 4 and 5, constituted chiefly of a pair of plate-like second side bar main bodies 621 and 622 provided face to face at given intervals and formed of a metal such as iron, a pressing means 70 provided in the gap between these second side bar main bodies 621 and 622, and a fixing member 623 that fixes the second side bar main bodies 621 and 622 to the other side edge of the transport path. The pressing means 70 is, as shown in FIGS. 6 and 7, constituted of a pressing member holder 71 having an opening 700 on the transport path side, a roller 76 provided projectably from the opening 700 within the pressing member holder 71, a pair of support member 74 movably supporting the roller 76 at its shaft 73, and a pair of spring members 75 pressing these supporting members 74 to push out the roller 76 to the transport path side. A guide roller 72 that guides the projecting motion of the roller 76 is also inserted between the roller 76 and the shaft 73.

The pressing means 70 of the second side bar 62 presses a tray delivered between the first side bar 61 and the second side bar 62 to bring the tray into engagement with the guide faces (the contact surfaces engageable with the tray in the plurality of rollers 611 provided to the first side bar main body 610 form the guide faces; see FIG. 4) of the first side bar 61, so that the trays with vegetables and fruits M placed thereon can be accurately delivered to proper positions of the respective measuring sections 31, 32 and 33 without causing any rocking motion of the trays with vegetables and fruits M placed thereon. Also, by the action of the plurality of rollers 611 provided to the first side bar 61 and the action of the roller 76 which constitutes part of the pressing means 70 of the second side bar 62, the frictional force accompanying the contact between the side bars 61 and 62 and the tray is reduced, and hence no difficulty may occur in the delivery performance of the tray in the transport path 20.

The above distributor and output monitoring detector provided in each measuring section are described below taking the case of the first measuring section 31.

Figure 8:
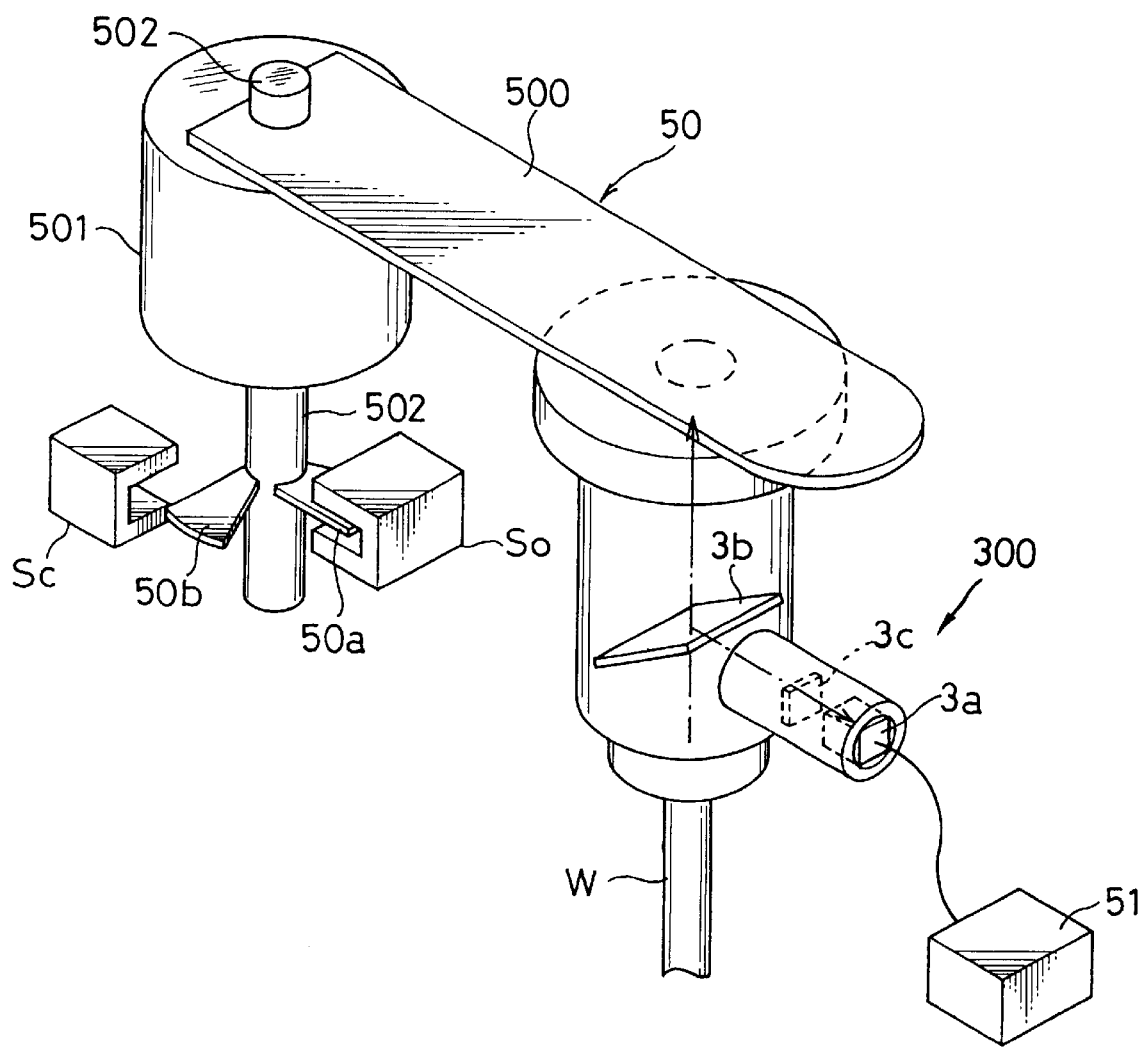
FIG. 8 is a cross-sectional view of a distributor, an output monitoring means and a shutter means in the non-destructive sugar content measuring apparatus according to Example 1.

First, the first distributor 3b disposed on the leading-end side of the optical fiber w inserted to the measurement-section-side light passage 31a in the measuring section 31 is, as shown in FIGS. 2 and 8, is constituted of a half mirror having been subjected to AR (anti-reflection) treatment on its light-emergent side. Part of the laser beam of wavelength $\lambda 1$ reflected from this mirror surface is led to the output monitoring detector 3a through a light diffusion plate 3c consisting of a combination of opal glass and frosted glass. Output signals corresponding to the amount of light detected there are amplified with the first monitoring amplifier 51 and at the same time inputted to the CPU 7 through the ADC 6 so as to be fed as data for measuring the sugar content. Here, the opal glass is a generic term of glass in which fine particles of different-type crystals (e.g., calcium fluoride) having a different refractive index have been dispersed to have milky color, and is also called milky glass. Also, since the first distributor 3b is constituted of a half mirror having been subjected to AR (anti-reflection) treatment on its light-emergent side, the laser beam is prevented from reflection on the light-emergent side and a laser beam having a stable beam shape can be introduced into the output monitoring detector 3a.

To also describe the shutter means provided in each measuring section, taking the case of that of the first measuring section 31, it is constituted chiefly of, as shown in FIGS. 2 and 8, a shielding plate 500 which is so provided as to be rotatable around a shaft on its base end side and swing horizontally on its leading end side, and opens or closes the optical path of the laser beam; a stepping motor 501 which is attached to the shielding plate 500 on its base end side, and rotates the shielding plate 500 on its base end side to cause the shielding plate 500 to swing on its leading end side up to the position where the optical path is opened or closed; and position sensors So and Sc which sense each position at which the shielding plate 500 stands still when the optical path is opened or closed, via two blade members 50a and 50b attached at the lower side of a rotary shaft 502 of the shielding plate 500.

Figure 9A:
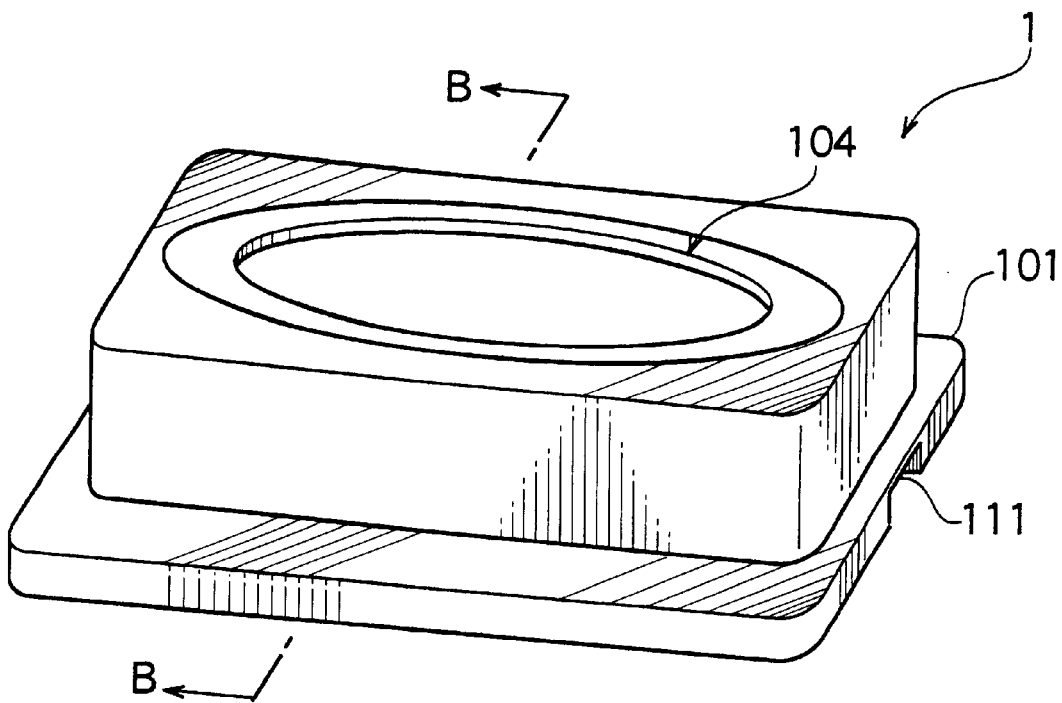
FIG. 9(A) is a perspective view of a tray to be delivered to the non-destructive sugar content measuring apparatus according to Example 1.
Figure 9B:
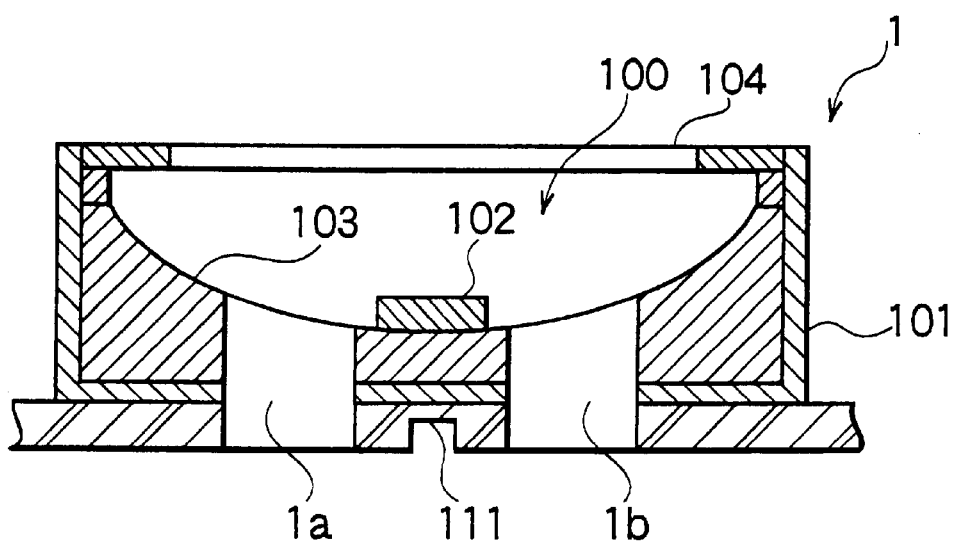
FIG. 9(B) is a cross-sectional view along the line B—B in FIG. 9(A).

As for the trays 1 delivered into this non-destructive sugar content measuring apparatus, they are, as shown in FIGS. 9(A) and 9(B), each constituted chiefly of a tray main body 101 made of black ABS (acrylonitrile-butadiene-styrene) resin, and having a rectangular holder 100 and a linear recession 111 which is provided at the bottom (under side) of the tray and is loosely fitted to the linear projection 10; a holding-part main body 103 comprised of NEOSPONGE rubber (trade name; available from San-Esu Rubber Co.), which is received in the holder 100 of the tray main body 101 and is provided at the center thereof with a holding part 102 made of urethane sponge; and a retainer 104 made of neoprene rubber, which is provided above the holding-part main body 103 and comes into contact with the periphery of a vegetable or fruit M to keep holding it.

In the non-destructive sugar content measuring apparatus according to Example 1, constituted as described above, a tray 1 on which a fruit M is placed in the same manner as in conventional apparatus is delivered into, e.g., the first measuring section 31, where as shown in FIG. 2 the shutter means 50 is moved and the laser beam of wavelength λ1 is made incident on the fruit M through the measurement-section-side light passage 31a and tray-side light passage 1a and at the same time the light emergent from the fruit M enters the detector 30 through the tray-side light passage 1b and measurement-section-side light passage 31b. Subsequently, the light emergent from the fruit M is likewise detected also in the second measuring section 32 and the third measuring section 33 to measure the sugar content. Incidentally, such measurement is so designed as to be made in a dark room as shown in FIG. 1.

In this non-destructive sugar content measuring apparatus, the standard deviations Δλ1, Δλ2 and Δλ3 of wavelength variations in the laser beams of wavelength λ1 (λ1=880 nm), wavelength λ2 (λ2=910 nm) and wavelength λ3 (λ3=930 nm), emitted from the first light source 41, second light source 42 and third light source 43, respectively, are all kept smaller than 0.057 nm as stated above, and the fluctuation of wavelength in each laser beam that may obstruct the measurement reproducibility is so small that the use of this apparatus enables measurement of the sugar content at an error within plus-minus 0.5 brix whenever the same vegetables and fruits kept at a constant temperature are measured.

EXAMPLE 2

Figure 10:
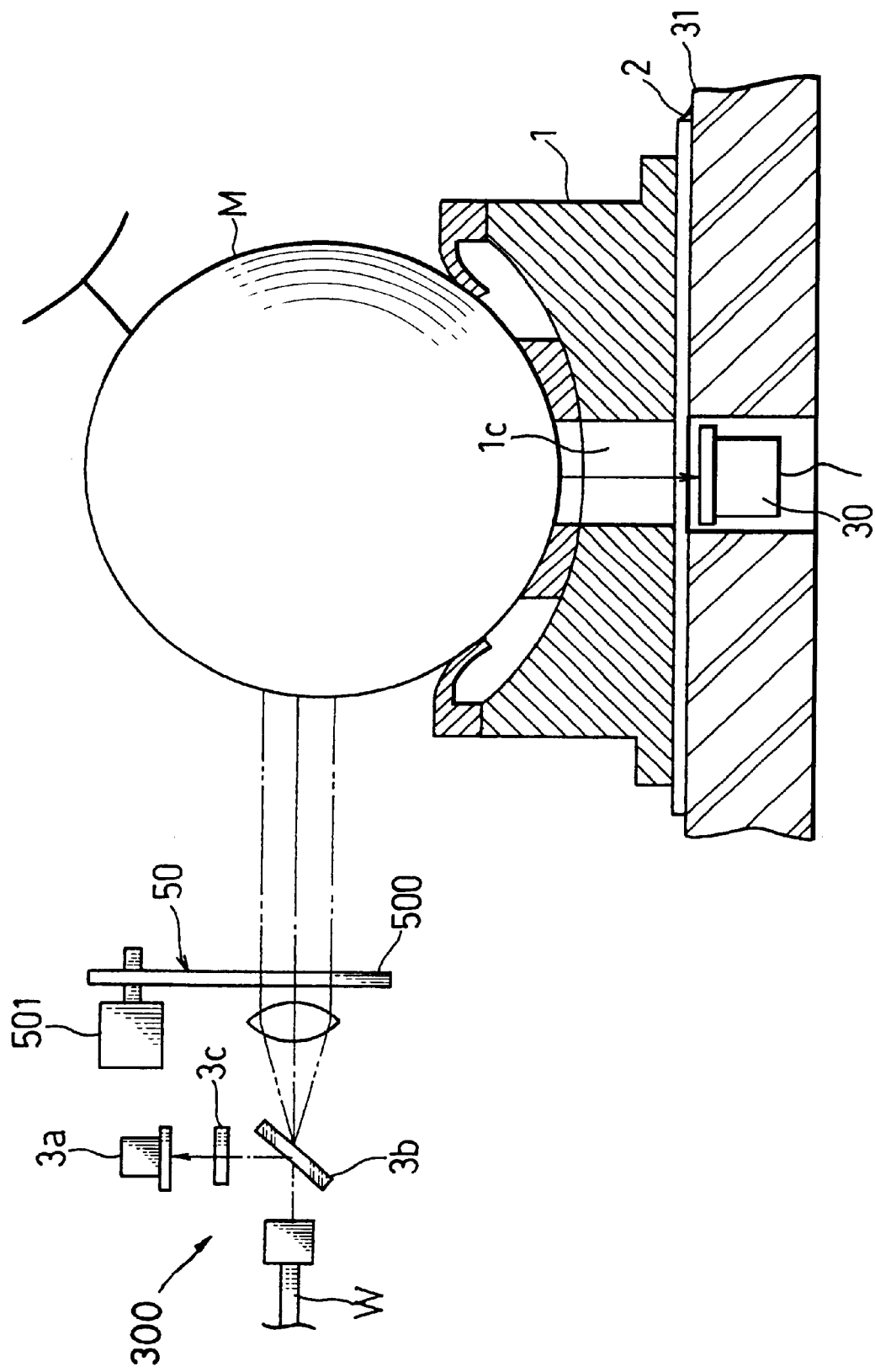
FIG. 10 is a cross-sectional illustration of the positional relation between a first measuring section and a tray delivered onto the first measuring section in a non-destructive sugar content measuring apparatus according to Example 2.
Figure 11:
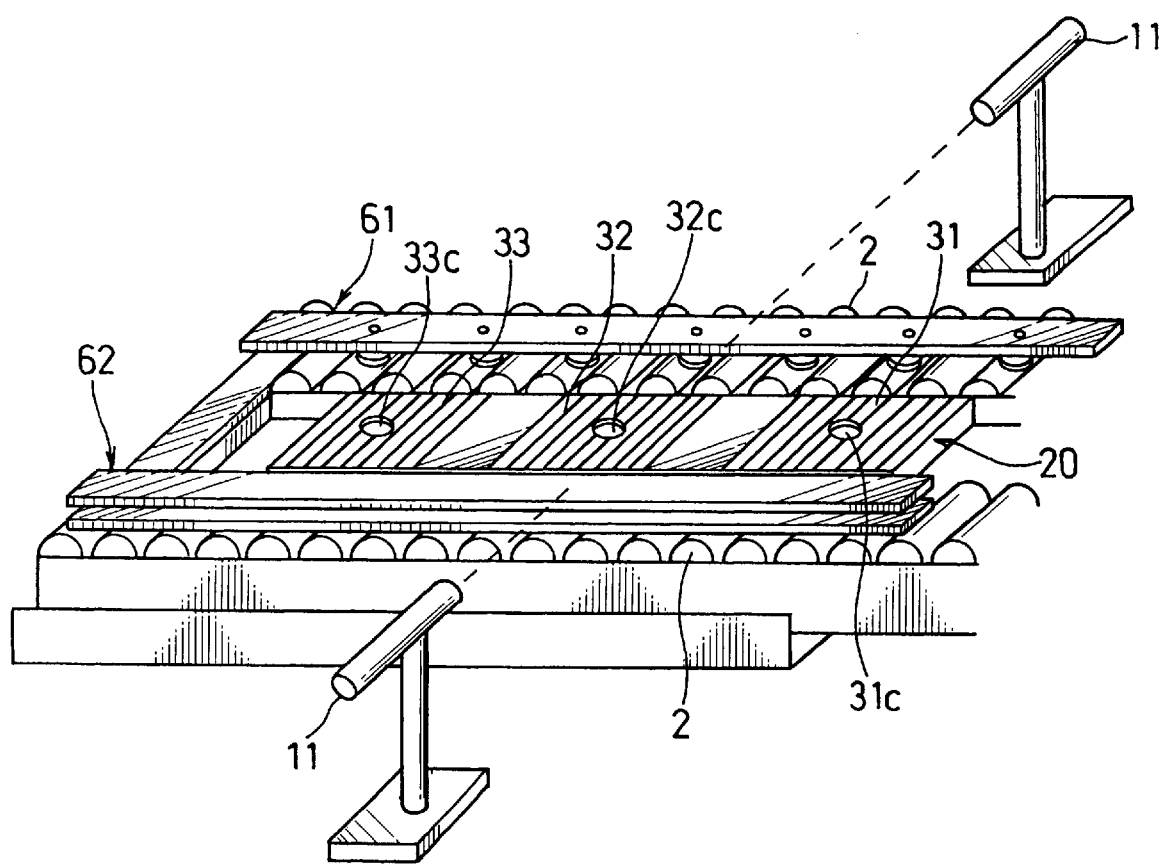
FIG. 11 is a perspective illustration of the main part of the non-destructive sugar content measuring apparatus according to Example 2.

FIGS. 10 to 11 shows a non-destructive sugar content measuring apparatus according to Example 2, which is suited for the measurement on muskmelons or oranges having a little thinner rinds than those in the apparatus according to Example 1.

More specifically, this non-destructive sugar content measuring apparatus is constituted chiefly of a transport path 201 provided in its lengthwise direction with a transport means 2 such as a roller conveyor or belt conveyor which delivers trays 1 on which vegetables and fruits M such as muskmelons are placed; a first measuring section 31, a second measuring section 32 and a third measuring section 32 which are consecutively disposed in the transport path 20 at given intervals; a first light source outside illustration which emits a laser beam of wavelength λ1 (λ1=860 nm) to a vegetable or fruit M delivered to the first measuring section 31, so as to make the laser beam enter it from its one lateral side through an optical fiber w; a second light source outside illustration which emits a laser beam of wavelength λ2 (λ2=880 nm) to a vegetable or fruit M delivered to the second measuring section 32, so as to make the laser beam enter it from its one lateral side through an optical fiber; a third light source outside illustration which emits a laser beam of wavelength λ3 (λ3=910 nm) to a vegetable or fruit M delivered to the third measuring section 33, so as to make the laser beam enter it from its one lateral side through an optical fiber; a first distributor 3b which is provided on the leading-end side of the optical fiber w connected to the first light source and distributes part of the laser beam of wavelength λ1 to guide it to an output monitoring detector 3a; a second distributor (not shown) which is provided on the leading-end side of the optical fiber connected to the second light source and distributes part of the laser beam of wavelength λ2 to guide it to another output monitoring detector outside illustration; a third distributor (not shown) which is provided on the leading-end side of the optical fiber connected to the third light source and distributes part of the laser beam of wavelength λ3 to guide it to still another output monitoring detector outside illustration; shutter means outside illustration which are respectively provided on the laser beam emergent sides in the first measuring section 31, second measuring section 32 and third measuring section 33 and are movable in accordance with sensing signals sent from vegetables and fruits sensing means (not shown) (a shutter means 50 in the first measuring section 31 is shown in FIG. 10); detectors outside illustration which are also respectively disposed in the first measuring section 31, second measuring section 32 and third measuring section 33 and measure the amount of light of the respective laser beams of wavelengths λ1, λ2 and λ3, becoming emergent from the vegetables and fruits M (a detector 30 in the first measuring section 31 is shown in FIG. 10); a first monitoring amplifier and a first amplifier (both not shown) which are connected to the output monitoring detector 3a and the detector 30 in the first measuring section 31 and amplify output signals corresponding to the amount of detected light of each laser beam of wavelength λ1, outputted from these detectors; a second monitoring amplifier and a second amplifier (both not shown) which are connected to an output monitoring detector and a detector in the second measuring section 32 and amplify output signals corresponding to the amount of detected light of each laser beam of wavelength λ2, outputted from these detectors; a third monitoring amplifier and a third amplifier (both not shown) which are connected to an output monitoring detector and a detector in the third measuring section 33 and amplify output signals corresponding to the amount of detected light of each laser beam of wavelength λ3, outputted from these detectors; an ADC (analog-digital converter) which are connected to these amplifiers and converts their analog output signals into digital signals; and a CPU which arithmetically operates the digital signals sent from this ADC, to calculate the sugar content of the vegetables and fruits M.

First, as the first light source, second light source and third light source outside illustration, DBR lasers, which are semiconductor lasers having been made vertically single-mode by means of a diffraction grating, are respectively used. Also, these light sources are disposed on a table (not shown) installed via an absorption rubber which absorbs vibrations, and are so regulated that any vibrations coming about in the surroundings do not travel to the light sources. At the same time, support members (not shown) which support the optical fibers w are also provided with the absorption rubber between the supporting members and the optical fibers w, and are so regulated that any vibrations do not travel to the optical fibers w. Also, constant-current power sources having a current stability of 0.1 mA are connected to power sources of the first light source, second light source and third light source, and the optical fibers w connected to the light sources are kept obliquely cut at their ends on the laser beam incident side so that the reflection of laser beams which occurs at the optical fiber ends on the laser beam incident side may no longer be backward directed to the light sources.

Here, with regard to the laser beams of wavelength λ1 (λ1=850 nm), wavelength λ2 (λ2=880 nm) and wavelength λ3 (λ3=910 nm), emitted from the first light source, second light source and third light source, respectively, their wavelengths were monitored and the standard deviations Δλ1, Δλ2 and Δλ3 of wavelength variations in the wavelengths λ1, λ2 and λ3 were determined to find that they were smaller than 0.060 nm in all the wavelengths λ1, λ2 and λ3.

Then, the first measuring section 31, second measuring section 32 and third measuring section 33 are, as shown in FIG. 11, consecutively disposed in the transport path 20 in its lengthwise direction and at given intervals. In the measuring sections 31, 32 and 33, measurement-section-side light passages 31c and 32c and 32c, respectively, are provided openly along the transport path 20 in its lengthwise direction, and the measuring sections are also respectively provided with the vegetables and fruits sensing means which sense the presence or absence of vegetables and fruits delivered to come to the measuring sections and output the detected signals to the shutter means (a vegetables and fruits sensing means 11 provided in the first measuring section 31 is shown in FIG. 11). Also, on the both sides of the transport path 20 along which the first measuring section 31, second measuring section 32 and third measuring section 33 are disposed, a first side bar 61 and a second side bar 62 which serve as a delivery position control means having the same construction as in the apparatus according to Example 1 are provided.

To describe the distributor, output monitoring detector and shutter means mentioned above, taking the case of the first measuring section 31, first, the first distributor 3b disposed in the measuring section 31 is, as shown in FIG. 10, is constituted of a half mirror having been subjected to AR (anti-reflection) treatment on its light-emergent side. Part of the laser beam of wavelength λ1 reflected from this mirror surface is led to the output monitoring detector 3a through a light diffusion plate 3c consisting of a combination of opal glass and frosted glass. Output signals corresponding to the amount of light detected there are amplified with the first monitoring amplifier and at the same time inputted to the CPU through the ADC so as to be fed as data for measuring the sugar content. Also, the shutter means 50 provided in the measuring section 31 is constituted chiefly of, as shown in FIG. 10, a shielding plate 500 which is so provided as to be rotatable around a shaft on its base end side and swing on its leading end side, and opens or closes the optical path of the laser beam; a stepping motor 501 which is attached to the shielding plate 500 on its base end side, and rotates the shielding plate 500 on its base end side to cause the shielding plate 500 to swing on its leading end side up to the position where the optical path is opened or closed; and a pair of position sensors (not shown) which is provided in the vicinity of the part where the shielding plate 500 swings to change its position and sense each position at which the shielding plate 500 stands still when the optical path is opened or closed.

Figure 12A:
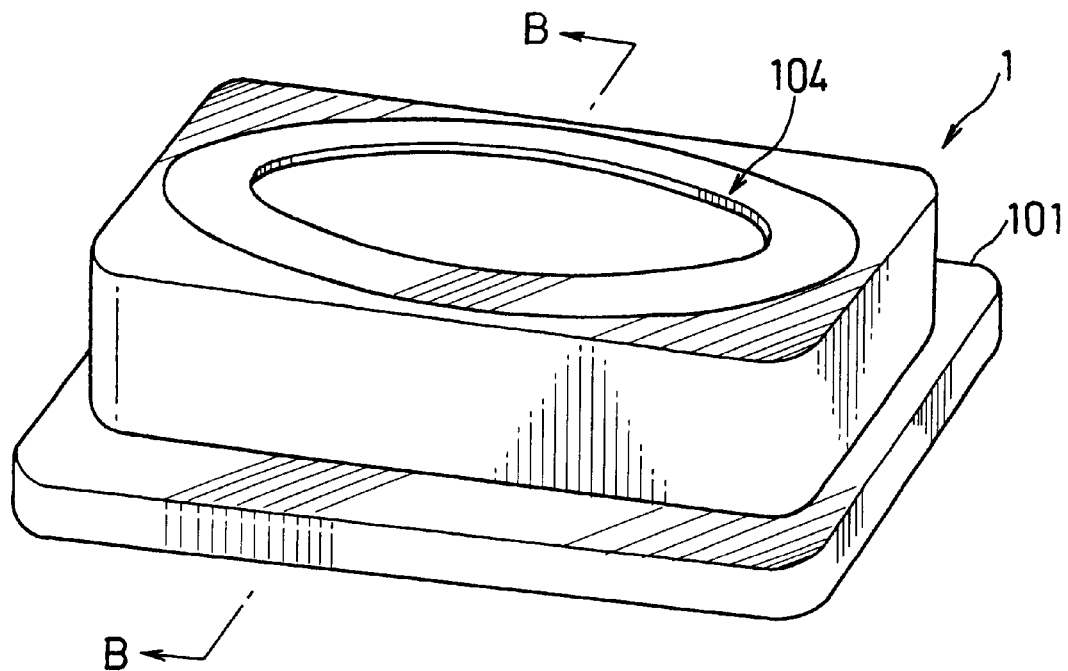
FIG. 12(A) is a perspective view of a tray to be delivered to the non-destructive sugar content measuring apparatus according to Example 2.
Figure 12B:
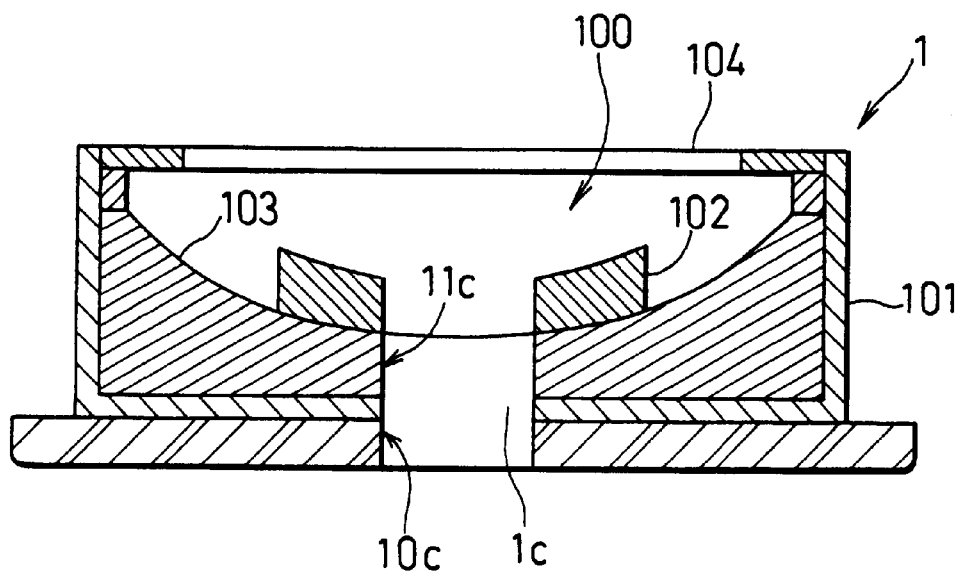
FIG. 12(B) is a cross-sectional view along the line B—B in FIG. 12(A).

As for the trays 1 delivered into this non-destructive sugar content measuring apparatus, they are, as shown in FIGS. 12(A) and 12(B), each constituted chiefly of a tray main body 101 made of black ABS (acrylonitrile-butadiene-styrene) resin, and having a rectangular holder 100 and a circular opening 10c provided at the bottom side of the tray to constitute a tray-side light passage 1c; a holding-part main body 103 comprised of NEOSPONGE rubber (trade name; available from San-Esu Rubber Co.), which is received in the holder 100 of the tray main body 101 and is provided, around the opening 11c at the center thereof, with a holding part 102 made of urethane sponge; and a retainer 104 made of neoprene rubber, which is provided above the holding-part main body 103 and comes into contact with the periphery of a vegetable or fruit M to keep holding it.

In the non-destructive sugar content measuring apparatus according to Example 2, constituted as described above, a tray 1 on which a fruit M is placed in the same manner as in conventional apparatus is delivered into, e.g., the first measuring section 31, where as shown in FIG. 10 the shutter means 50 is moved and the laser beam of wavelength λ1 is made incident on the fruit M and at the same time the light emergent from the fruit M enters the detector 30 through the tray-side light passage 1c. Subsequently, the light emergent from the fruit M is likewise detected also in the second measuring section 32 and the third measuring section 33 to measure the sugar content. Incidentally, such measurement is so designed as to be made in a dark room as in the non-destructive sugar content measuring apparatus according to Example 1, shown in FIG. 1.

In this non-destructive sugar content measuring apparatus, the standard deviations Δλ1, Δλ2 and Δλ3 of wavelength variations in the laser beams of wavelength λ1 (λ1=850 nm), wavelength λ2 (λ2=880 nm) and wavelength λ3 (λ3=920 nm), emitted from the first light source, second light source and third light source, respectively, are all kept smaller than 0.060 nm as stated above, and the fluctuation of wavelength in each laser beam that may obstruct the measurement reproducibility is so small that the use of this apparatus enables measurement of the sugar content at an error within plus-minus 0.5 brix whenever the same vegetables and fruits kept at a constant temperature are measured.

What is claimed is:

1. A non-destructive sugar content measuring apparatus comprising a plurality of trays on which vegetables and fruits are to be placed, a transport means for successively delivering the trays at appropriate intervals, and first, second and third measuring sections provided in the course of a transport path and at which laser beams having wavelengths λ1, λ2 and λ3 are respectively made incident on each vegetable or fruit and the amount of light of each laser beam emergent from the vegetable or fruit is measured with a detector provided at each measuring section and at the same time the absorbance of each laser beam is determined from the amount of incident light made incident on the vegetable or fruit and the amount of detected light which has been measured with the detector, to measure the sugar content of the vegetables and fruits on the basis of each absorbance thus determined wherein;

the wavelengths λ1, λ2 and λ3 of said laser beams satisfy the conditions of:

$$860 \text{ nm} \leq \text{wavelength } \lambda1 < 900 \text{ nm},$$

$$900 \text{ nm} \leq \text{wavelength } \lambda2 \leq 920 \text{ nm},$$

$$920 \text{ nm} < \text{wavelength } \lambda3 \leq 960 \text{ nm},$$

and, where standard deviations of wavelength variations in the wavelengths λ1, λ2 and λ3 are represented by Δλ1, Δλ2 and Δλ3, respectively, satisfy the condition of the following mathematical expression (1):

$$[f1(\lambda1) \times \Delta\lambda1 + f2(\lambda2) \times \Delta\lambda2 + f3(\lambda3) \times \Delta\lambda3] < 0.5 \text{ brix} \qquad (1);$$

in which mathematical expression (1), f1(λ1), f2(λ2) and f3(λ3) respectively represent sugar content variation functions (brix/nm) determined from sugar content variation curves showing the relationship between the wavelength variations in the wavelengths λ1, λ2 and λ3 and the sugar content variations that accompany the former.

2. The non-destructive sugar content measuring apparatus according to claim 1, wherein the f1(λ1), f2(λ2) and f3(λ3) are represented by the following mathematical expressions f1(λ1), f2(λ2) and f3(λ3):

$$f1(\lambda1) = -20182.34 + 69.83868 \times (\lambda1) - 0.08055962 \times (\lambda1)^2 + 3.097853 \times 10^{-5} \times (\lambda1)^3,$$

$$f2(\lambda2) = 151409.7 - 499.542 \times (\lambda2) + 0.5493413 \times (\lambda2)^2 - 2.013521 \times 10^{-4} \times (\lambda2)^3,$$

$$f3(\lambda3) = 8990.066 - 28.1535 \times (\lambda3) + 0.02940324 \times (\lambda3)^2 - 1.023846 \times 10^{-5} \times (\lambda3)^3.$$

3. The non-destructive sugar content measuring apparatus according to claim 1 or 2, wherein the standard deviations Δλ1, Δλ2 and Δλ3 of the wavelength variations in the wavelengths λ1, λ2 and λ3 are each 0.057 nm or smaller.

4. The non-destructive sugar content measuring apparatus according to claim 1 or 2, wherein;

the wavelengths λ1, λ2 and λ3 of said laser beams satisfy the conditions of:

860 nm ≤ wavelength λ1 ≤ 890 nm, 900 nm ≤ wavelength λ2 ≤ 915 nm, 920 nm ≤ wavelength λ3 ≤ 940 nm, and the standard deviations Δλ1, Δλ2 and Δλ3 of the wavelength variations in the wavelengths λ1, λ2 and λ3 are each 0.064 nm or smaller.

5. The non-destructive sugar content measuring apparatus according to claim 1 or 2, wherein the wavelength λ1, λ2 and λ3 of said laser beams satisfy the conditions of λ1=880 nm, wavelength λ2=910 nm and wavelength λ3=930 nm, and the standard deviations Δλ1, Δλ2 and Δλ3 of the wavelength variations in the wavelengths λ1, λ2 and λ3 are each 0.072 nm or smaller.

6. A non-destructive sugar content measuring apparatus comprising a plurality of trays on which vegetables and fruits are to be placed, a transport means for successively delivering the trays at appropriate intervals, and first, second and third measuring sections provided in the course of a transport path and at which laser beams having wavelengths λ1, λ2 and λ3 are respectively made incident on each vegetable or fruit and the amount of light of each laser beam emergent from the vegetable or fruit is measured with a detector provided at each measuring section and at the same time the absorbance of each laser beam is determined from the amount of incident light made incident on the vegetable or fruit and the amount of detected light which has been measured with the detector, to measure the sugar content of the vegetables and fruits on the basis of each absorbance thus determined wherein;

the wavelengths λ1, λ2 and λ3 of said laser beams satisfy the conditions of:

800 nm ≤ wavelengths λ1, λ2 < 900 nm, 900 nm ≤ wavelength λ3 ≤ 920 nm, the wavelengths λ1 and λ2 having a wavelength distance between them of 10 nm or larger;

and, where standard deviations of wavelength variations in the wavelengths λ1, λ2 and λ3 are represented by Δλ1, Δλ2 and Δλ3, respectively, satisfy the condition of the following mathematical expression (1):

$$[f1(\lambda 1) \times \Delta\lambda 1 + f2(\lambda 2) \times \Delta\lambda 2 + f3(\lambda 3) \times \Delta\lambda 3] < 0.5 \text{ brix} \qquad (1);$$

in which mathematical expression (1), f1(λ1), f2(λ2) and f3(λ3) respectively represent sugar content variation functions (brix/nm) determined from sugar content variation curves showing the relationship between the wavelength variations in the wavelengths λ1, λ2 and λ3 and the sugar content variations that accompany the former.

7. The non-destructive sugar content measuring apparatus according to claim 6, wherein the f1(λ1), f2(λ2) and f3(λ3) are represented by the following mathematical expressions f(λ);

In the case of 800 nm ≤ wavelengths λ1, λ2 ≤ 820 nm, $$f(\lambda) = -74458.74 + 277.6852 \times \lambda - 0.345206 \times \lambda^2 + 1.43052 \times 10^{-4} \times \lambda^3,$$

In the case of 820 nm < wavelengths λ1, λ2 ≤ 840 nm, $$f(\lambda) = -270722.5 + 972.2863 \times \lambda - 1.163856 \times \lambda^2 + 4.643458 \times 10^{-4} \times \lambda^3,$$

In the case of 840 nm < wavelengths λ1, λ2, λ3 ≤ 920 nm, $$f(\lambda) = 8564.296 - 29.36077 \times \lambda + 0.033502 \times \lambda^2 - 1.272059 \times 10^{-6} \times \lambda^3.$$

8. The non-destructive sugar content measuring apparatus according to claim 6 or 7, wherein the standard deviations Δλ1, Δλ2 and Δλ3 of the wavelength variations in the wavelengths λ1, λ2 and λ3 are each 0.060 nm or smaller.

9. The non-destructive sugar content measuring apparatus according to claim 1, 2, 6 or 7, wherein light sources of said laser beams are semiconductor lasers having been made vertically single-mode by means of a diffraction grating.

10. The non-destructive sugar content measuring apparatus according to claim 9, wherein the light sources of said laser beams are DBR, DFB or fiber grating lasers.

11. The non-destructive sugar content measuring apparatus according to claim 1, 2, 6 or 7, wherein said laser beams of wavelengths λ1, λ2 and λ3 are made incident on the vegetables and fruits through optical fibers, and the optical fibers are kept obliquely cut at their ends on the laser beam incident side.

12. The non-destructive sugar content measuring apparatus according to claim 1, 2, 6 or 7, wherein light sources of said laser beams are constituted of semiconductor lasers having been made vertically single-mode, or vertical multimode oscillation type semiconductor lasers, and their power sources are constituted of constant-current power sources having a current stability of 0.1 mA.

\* \* \* \* \*